United States Patent
Fathallah et al.

(10) Patent No.: US 7,945,452 B2
(45) Date of Patent: May 17, 2011

(54) USER INTERFACE IMPROVEMENTS FOR MEDICAL DEVICES

(75) Inventors: Marwan A. Fathallah, Mundelein, IL (US); Heather J. Barnes, Raleigh, NC (US); Kristine T. Delano, Windham, ME (US); Amy B. Magurno, Raleigh, NC (US); Eric R. Wald, Westbrook, ME (US); Corinna S. Paine Proctor, Raleigh, NC (US); Kevin O. Roughton, Saco, ME (US); Kevin Barkan, Durham, NC (US); John W. Huang, Hillsborough, CA (US); Raymond P. Silkaitis, Lake Forest, IL (US); Mihaela Cozmi, Gilroy, CA (US); Glenn Davis, Grayslake, IL (US); Bernardino Rubalcaba, Jr., Escondido, CA (US); Katalin M. Schroeder, Kenosha, WI (US); Suzanne Willey, San Diego, CA (US)

(73) Assignee: Hospira, Inc., Lake Forest, IL (US)

( * ) Notice: Subject to any disclaimer, the term of this patent is extended or adjusted under 35 U.S.C. 154(b) by 1687 days.

(21) Appl. No.: 11/103,235

(22) Filed: Apr. 11, 2005

(65) Prior Publication Data
US 2006/0229557 A1     Oct. 12, 2006

(51) Int. Cl.
*G06Q 10/00* (2006.01)
*G06Q 50/00* (2006.01)
(52) U.S. Cl. .......................................................... 705/2
(58) Field of Classification Search .................. 705/2, 3, 705/4; 141/27; 273/148 R; 345/123, 786, 345/77; 368/10; 395/157; 604/65; 600/300; 700/265; 58/50 R; 340/608
See application file for complete search history.

(56) References Cited

U.S. PATENT DOCUMENTS

| | | | |
|---|---|---|---|
| 3,838,565 A * | 10/1974 | Carlyle | .......................... 368/84 |
| 4,756,706 A | 7/1988 | Kerns et al. | |
| 4,898,578 A | 2/1990 | Rubalcaba, Jr. | |
| 5,041,086 A | 8/1991 | Koenig et al. | |
| 5,233,571 A * | 8/1993 | Wirtschafter | .................. 368/10 |
| 5,276,610 A | 1/1994 | Maeda et al. | |
| 5,319,363 A | 6/1994 | Welch et al. | |
| D352,778 S | 11/1994 | Irvin et al. | |
| 5,429,602 A | 7/1995 | Hauser | |
| 5,445,621 A | 8/1995 | Poli et al. | |
| 5,485,408 A | 1/1996 | Blomquist | |
| 5,495,566 A * | 2/1996 | Kwatinetz | ..................... 715/785 |

(Continued)

FOREIGN PATENT DOCUMENTS
EP     1 197 178 A1    4/2002
(Continued)

*Primary Examiner* — Gerald J. O'Connor
*Assistant Examiner* — John A Pauls
(74) *Attorney, Agent, or Firm* — Michael R. Crabb

(57) ABSTRACT

A method and apparatus is disclosed for operating a medical device with a screen having an improved graphical user interface, which selectively reallocates screen display for both single and multi-channel pumps. Channel indicators associate operation information with a specific delivery channel. Patient or drug order verification is facilitated with a rendering of the patient or the entire drug order/label on the screen. Decimal numbers are presented in vertically offset decimal format. A dual function button cancels the current operation and, after a delay, clears entered parameters. An area sensitive scrollbar cycles through information at various speeds. Screen brightness is adjusted based on an ambient light detector. A screen saver mode activates based on several operating conditions. The screen is incorporated in a removable user interface.

23 Claims, 32 Drawing Sheets

U.S. PATENT DOCUMENTS

| | | | |
|---|---|---|---|
| 5,496,273 A | 3/1996 | Pastrone et al. | |
| 5,507,412 A | 4/1996 | Ebert et al. | |
| 5,522,798 A | 6/1996 | Johnson et al. | |
| 5,547,470 A | 8/1996 | Johnson et al. | |
| 5,558,638 A | 9/1996 | Evers et al. | |
| 5,626,151 A | 5/1997 | Linden | |
| 5,681,285 A | 10/1997 | Ford et al. | |
| 5,685,844 A | 11/1997 | Marttila | |
| 5,713,856 A * | 2/1998 | Eggers et al. | 604/65 |
| 5,718,562 A | 2/1998 | Lawless et al. | |
| 5,772,635 A | 6/1998 | Dastur et al. | |
| 5,781,442 A | 7/1998 | Engleson et al. | |
| 5,782,805 A | 7/1998 | Meinzer et al. | |
| 5,814,015 A | 9/1998 | Gargano et al. | |
| 5,864,330 A * | 1/1999 | Haynes | 715/856 |
| 5,935,099 A | 8/1999 | Peterson et al. | |
| 6,241,704 B1 | 6/2001 | Peterson et al. | |
| 6,269,340 B1 | 7/2001 | Ford et al. | |
| 6,337,675 B1 * | 1/2002 | Toffolo et al. | 345/77 |
| 6,544,228 B1 | 4/2003 | Heitmeier | |
| 6,689,091 B2 | 2/2004 | Bui et al. | |
| 6,738,052 B1 | 5/2004 | Manke et al. | |
| 6,793,625 B2 | 9/2004 | Cavallaro et al. | |
| 6,801,227 B2 | 10/2004 | Bocionek et al. | |
| 6,928,338 B1 * | 8/2005 | Buchser et al. | 700/265 |
| 2001/0014769 A1 * | 8/2001 | Bufe et al. | 600/300 |
| 2001/0044731 A1 | 11/2001 | Coffman et al. | |
| 2002/0003892 A1 | 1/2002 | Iwanaga | |
| 2002/0029776 A1 | 3/2002 | Blomquist | |
| 2002/0044059 A1 | 4/2002 | Reeder et al. | |
| 2002/0085952 A1 | 7/2002 | Ellingboe et al. | |
| 2002/0143580 A1 | 10/2002 | Bristol et al. | |
| 2002/0169636 A1 * | 11/2002 | Eggers et al. | 705/3 |
| 2003/0009244 A1 | 1/2003 | Engleson et al. | |
| 2003/0060765 A1 | 3/2003 | Campbell et al. | |
| 2003/0065537 A1 | 4/2003 | Evans | |
| 2003/0135087 A1 | 7/2003 | Hickle et al. | |
| 2003/0135388 A1 | 7/2003 | Martucci et al. | |
| 2003/0141981 A1 * | 7/2003 | Bui et al. | 340/608 |
| 2003/0158508 A1 | 8/2003 | DiGianfilippo et al. | |
| 2003/0233071 A1 | 12/2003 | Gillespie, Jr. et al. | |
| 2004/0104271 A1 | 6/2004 | Martucci et al. | |
| 2004/0119753 A1 * | 6/2004 | Zencke | 345/786 |
| 2004/0145114 A1 * | 7/2004 | Ippolito et al. | 273/148 R |
| 2004/0158193 A1 | 8/2004 | Bui et al. | |
| 2004/0172289 A1 * | 9/2004 | Kozic et al. | 705/2 |
| 2004/0193328 A1 | 9/2004 | Zaitsu et al. | |
| 2005/0182366 A1 | 8/2005 | Vogt et al. | |
| 2005/0279419 A1 * | 12/2005 | Tribble et al. | 141/27 |
| 2006/0042633 A1 | 3/2006 | Bishop et al. | |

FOREIGN PATENT DOCUMENTS

| | | | |
|---|---|---|---|
| WO | WO96/36389 | * 11/1996 | |

\* cited by examiner

| ON-SCREEN ITEM DESCRIPTION | ON-SCREEN ITEM ILLUSTRATION |
|---|---|
| BOLUS ICON |  56A |
| BASIC PROGRAM ICON |  56B |
| INTERMITTENT THERAPY ICON |  56C |
| MULTISTEP THERAPY ICON |  56D |
| TAPER THERAPY ICON |  56E |
| VARIABLE TIME THERAPY ICON |  56F |
| PIGGYBACK ICON |  56G |

| ON-SCREEN ITEM DESCRIPTION | ON-SCREEN ITEM ILLUSTRATION |
|---|---|
| EXCEEDS UPPER HARD LIMIT ICON |  57C |
| EXCEEDS LOWER HARD LIMIT ICON |  57D |
| EXCEEDS UPPER SOFT LIMIT ICON |  57A |
| EXCEEDS LOWER SOFT LIMIT ICON |  57B |
| OUTSIDE RULE SET ICON |  57E |

USER INTERFACE IMPROVEMENTS FOR MEDICAL DEVICES

BACKGROUND OF THE INVENTION

The present invention relates to medical devices. More particularly, this invention relates to medical devices that include graphical user interfaces.

The design of graphical user interfaces for use with medical devices is a challenging undertaking, as many needs must be met within strict design parameters as well as safety parameters. For instance, with multi-channel infusion pumps, existing user interfaces often have insufficient indicators to the user to visually indicate which channel is delivering what medication. Further, too often the user is presented with an overwhelming amount of information, impeding the interaction between the user and the user interface. Conversely, the opposite condition of having too little information presented to the user is often present in these existing user interfaces.

Modern medical devices, including medical pumps, can be complicated and time-consuming for caregivers to program. Medical facilities struggle to provide appropriate caregiver staffing levels and training while holding down the cost of medical care. Human errors in pump programming and other medication errors can have adverse or even deadly consequences for the patient. The need for an improved graphical interface is critical to maintain efficiency of patient care and to reduce potential clinical errors and thereby improve patient safety. The changing demographics of the clinician population has made current devices difficult to use and prone to causing errors, for example, nurses now tend to be older and there are fewer of them to take care of patients. Device interfaces that increase input efficiency and take into account the physical needs of the user, such as decreased visual acuity, are critical to improve clinician accuracy, patient safety and therapy.

It is therefore an object of this invention to provide a medical device with a screen saver mode, with multiple display options presented based on any number of operating conditions.

Another object of the present invention is to provide a medical device with an area sensitive scrollbar for cycling up and down through lists of selectable information at various speeds.

A further object of the present invention is to provide a medical device with a dual function clear and cancel button.

A further object of the present invention is to provide a medical device with a display that alternates between far and near views that provide the appropriate information to the clinician for monitoring and programming while allowing for minimal patient disruption and power consumption.

A further object of the present invention is to provide a medical device with a display screen that is large enough to display an image of the patient, a complete infusion order, or a drug container label for verification purposes.

These and other objects will be apparent to those skilled in the art.

SUMMARY OF THE INVENTION

A method and apparatus is disclosed for operating a medical device with a screen input/output device having an improved graphical user interface. The medical device includes an output screen that provides a large amount of information in an enlarged, consolidated, and user-friendly physical and logical arrangement for safe input of information, and an automatic alternate view with key information for monitoring the device visually from across the room.

The medical device includes a machine-readable input device for selecting a channel from one or more channels, by scanning in a machine-readable label associated with each channel. The graphical user interface reallocates screen display for a multi-channel infusion pump, and because of its size can even combine two or more displays onto a single common display screen upon connecting two or more medical devices together. Channel indicators associate on-screen programming, delivery, and alarm information with a delivery channel by using graphical depictions such as a channel indication icon or an infusion status icon. The infusion status icon graphically indicates the following types of delivery operation: basic therapy, piggyback (a secondary container for therapeutic agent connected to the IV line between the primary container and the pump), multi-step therapy, variable time therapy, intermittent therapy, taper therapy, and/or bolus delivery. A drip indicator icon provides an animated "raindrop shape" presented when a delivery is occurring.

Patient identification can be facilitated by displaying on the screen indicia identifying the patient, including but not limited to a rendering or digital photograph of the patient, patient name, an identification number or code, a bar code, or other indicia identifying the patient.

Decimal numbers are presented in offset decimal format where the digits presented to the right of the decimal are of smaller height with their bottom vertically offset, for example raised or lowered, from bottom of the digits to the left of the decimal.

"Explode" or "active" buttons, when pressed or otherwise actuated, activate or provide a standard data entry field that expands to a larger area for data entry when the button is selected.

A dual function clear/cancel button provides in a single button area the function of canceling the currently selected operation to return to the previous state, and after a delay, clearing all entered parameters.

An area sensitive scrollbar provides for smooth, quick, and efficient maneuvering or cycling through lists of selectable information at various speeds and in different directions.

The screen brightness is adjusted based on the feedback from an ambient light detector. A screen saver mode, with multiple display options, is displayed based on any number of operating conditions. The screen itself is designed to be incorporated in a removable user interface to the medical device.

The screen is large enough to display a complete infusion order comprising multiple therapeutic agents at one time and can even display all or a portion of a drug container label for verification purposes.

DETAILED DESCRIPTION OF THE PREFERRED EMBODIMENT

The present invention will be described as it applies to its preferred embodiment. It is not intended that the present invention be limited to the preferred embodiment. It is intended that the invention cover all modifications and alternatives that may be included within the scope of the appended claims.

Figure 1:
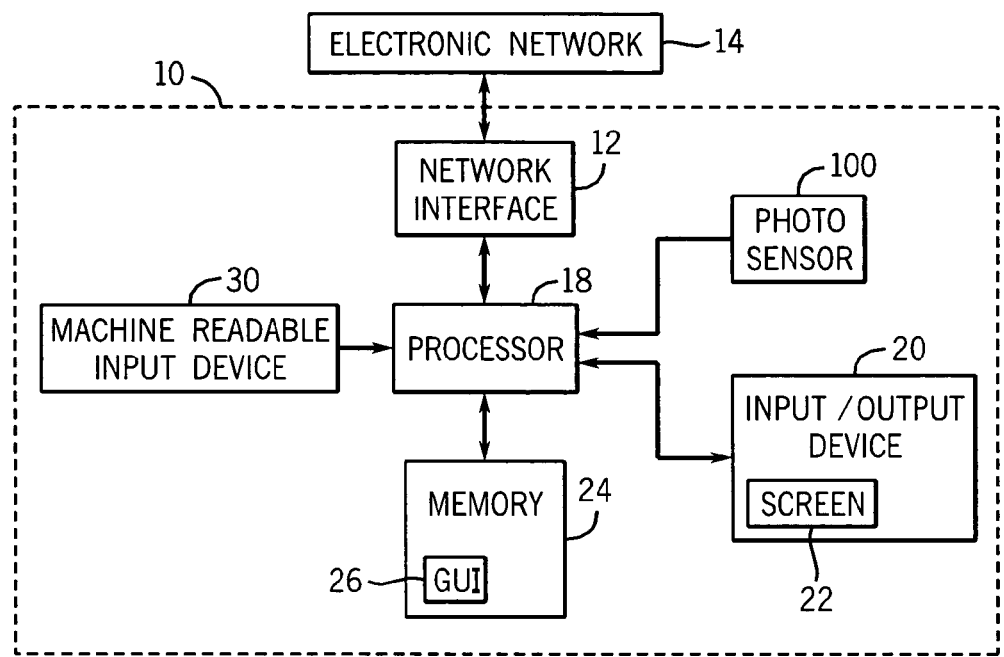
FIG. 1 is a schematic diagram of a medical device according to the present invention.

FIG. 1 is a schematic diagram illustrating several functional components of a medical pump 10 for implementing the present invention. Those of ordinary skill in the art will appreciate that the pump 10 includes many more components than those shown in FIG. 1. However, it is not necessary that all these components be shown in order to disclose an illustrative embodiment for practicing the present invention.

In the context of the present invention, the term "medical device" includes without limitation a device that acts upon a cassette, reservoir, vial, syringe, or tubing to convey medication or fluid to or from a patient (for example, an enteral pump, a parenteral infusion pump, a patient controlled analgesia (PCA) or pain management medication pump, or a suction pump), a monitor for monitoring patient vital signs or other parameters, or a diagnostic device.

Referring to FIGS. 2-6, for the purpose of exemplary illustration only, the medical device 10 is disclosed as an infusion pump. More particularly, the medical device 10 can be a single channel infusion pump 10A, a multi-channel infusion pump 10B, or some combination thereof.

Figure 3:
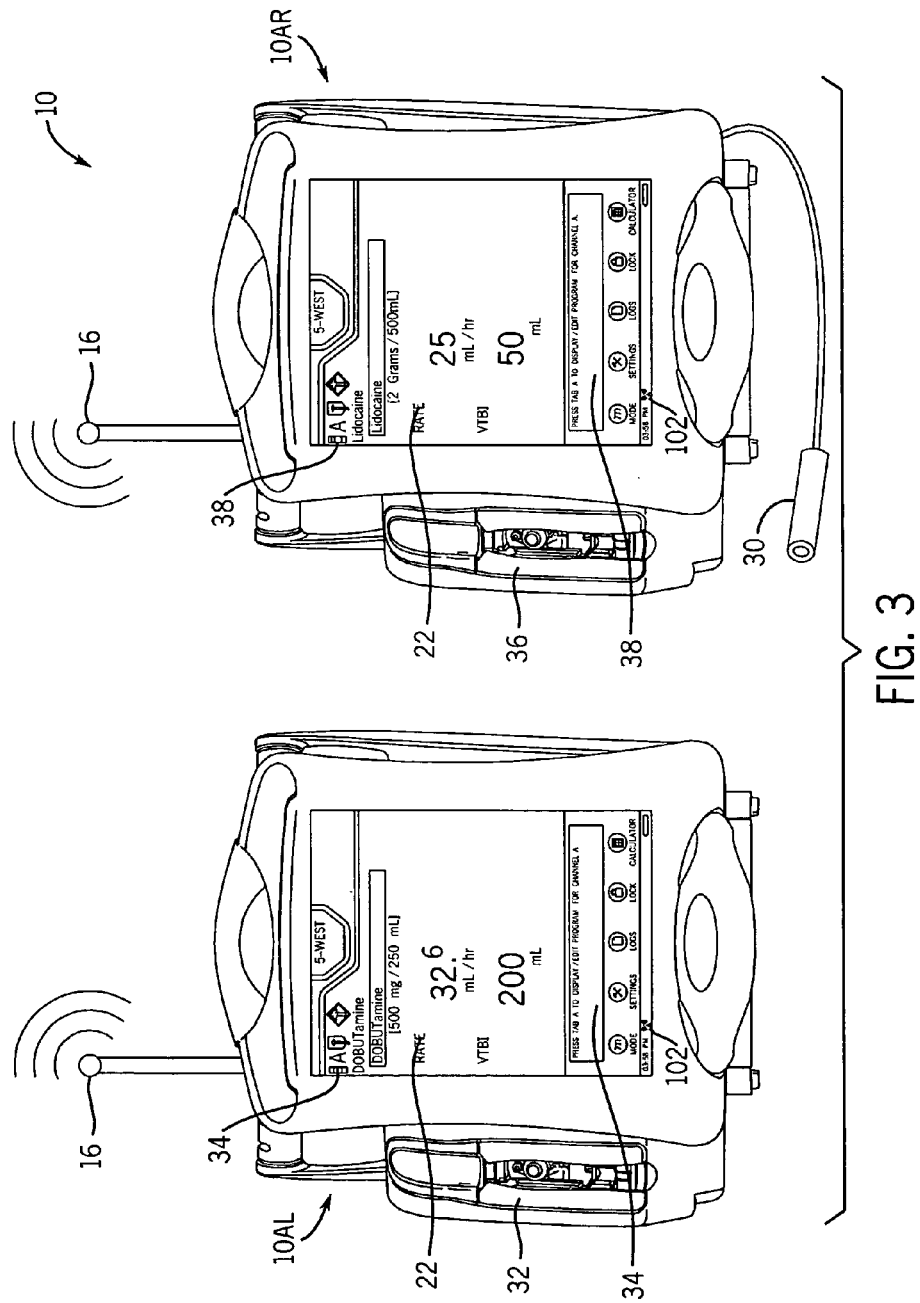
FIG. 3 is a perspective view of a first medical device communicating wirelessly with a second medical device and having a channel association feature according to the present invention.
Figure 4:
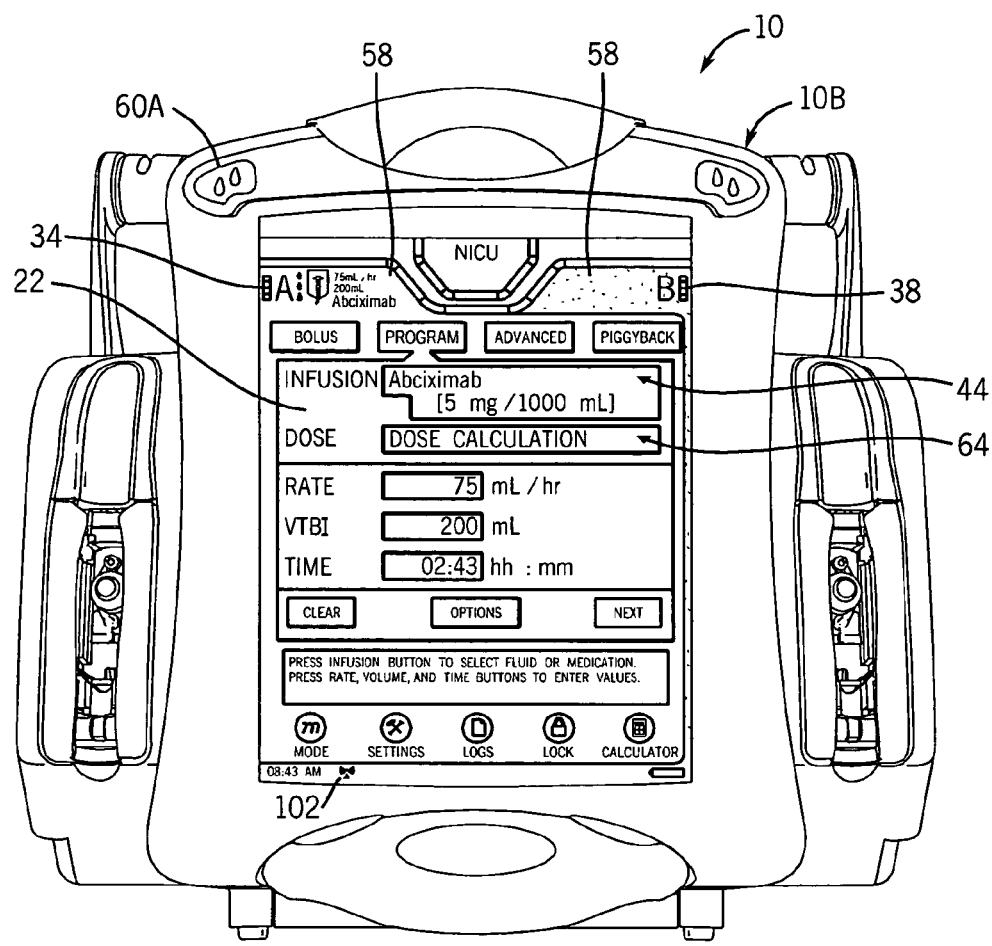
FIG. 4 is a front view of the multi-channel medical device of FIG. 2 showing additional features according to the present invention.

With reference to FIGS. 1 and 3 the pump style medical device 10 includes a network interface 12 for connecting the medical device 10 to an electronic network 14. The electronic network 14 can be a completely wireless network, a completely hard-wired network, or some combination thereof. As best seen in FIG. 3, where a wireless connection to the electronic network 14 is desired, network interface 12 operates an antenna 16 for wireless connection to the electronic network 14. The antenna 16 can be project outside the device 10 or be enclosed within the housing of the device.

A processor 18 is included in the medical device 10 and performs various operations described in greater detail below. The input/output device 20 allows the user to receive output from the medical device 10 and/or input information into the medical device 10. Those of ordinary skill in the art will appreciate that input/output device 20 may be provided as a single device such as a touch screen 22, or as a separate display device and a separate input device (not shown). In the preferred embodiment, the display screen 22 of the medical pump 10 is a thin film transistor active matrix color liquid crystal display with a multi-wire touch screen. The screen 22 measures approximately 8.5 in. (22 cm) diagonally and has a rectangular working area approximately 5 in. (13 cm) wide by 7 in. (18 cm) long. A membrane generally impermeable to fluids overlays the display screen 22 so the user can press on images of keys or buttons on the underlying screen with wet gloves, dry gloves or without gloves to trigger an input.

A memory 24 communicates with the processor 18 and stores code and data necessary for the processor 18 to perform the functions of the medical device 10. More specifically, the memory 24 stores multiple programs formed in accordance with the present invention for various functions of the medical device 10 including a graphical user interface program 26 with multiple subparts described in greater detail below.

Figure 5:
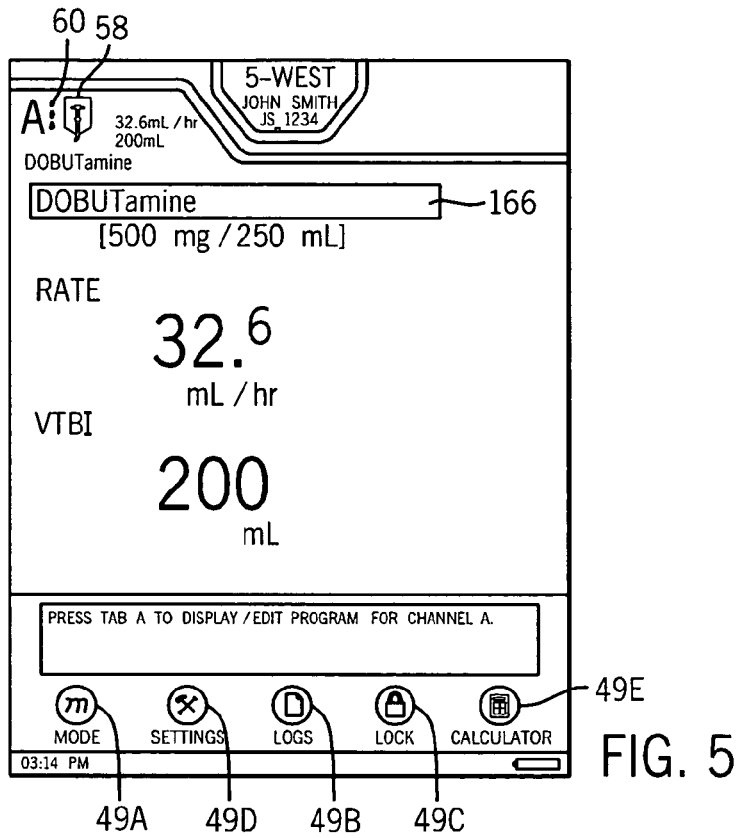
FIG. 5 is a screen shot of a single channel medical device with a screen display that is adapted to be displayed and viewed from afar during normal delivery of fluid.
Figure 6:
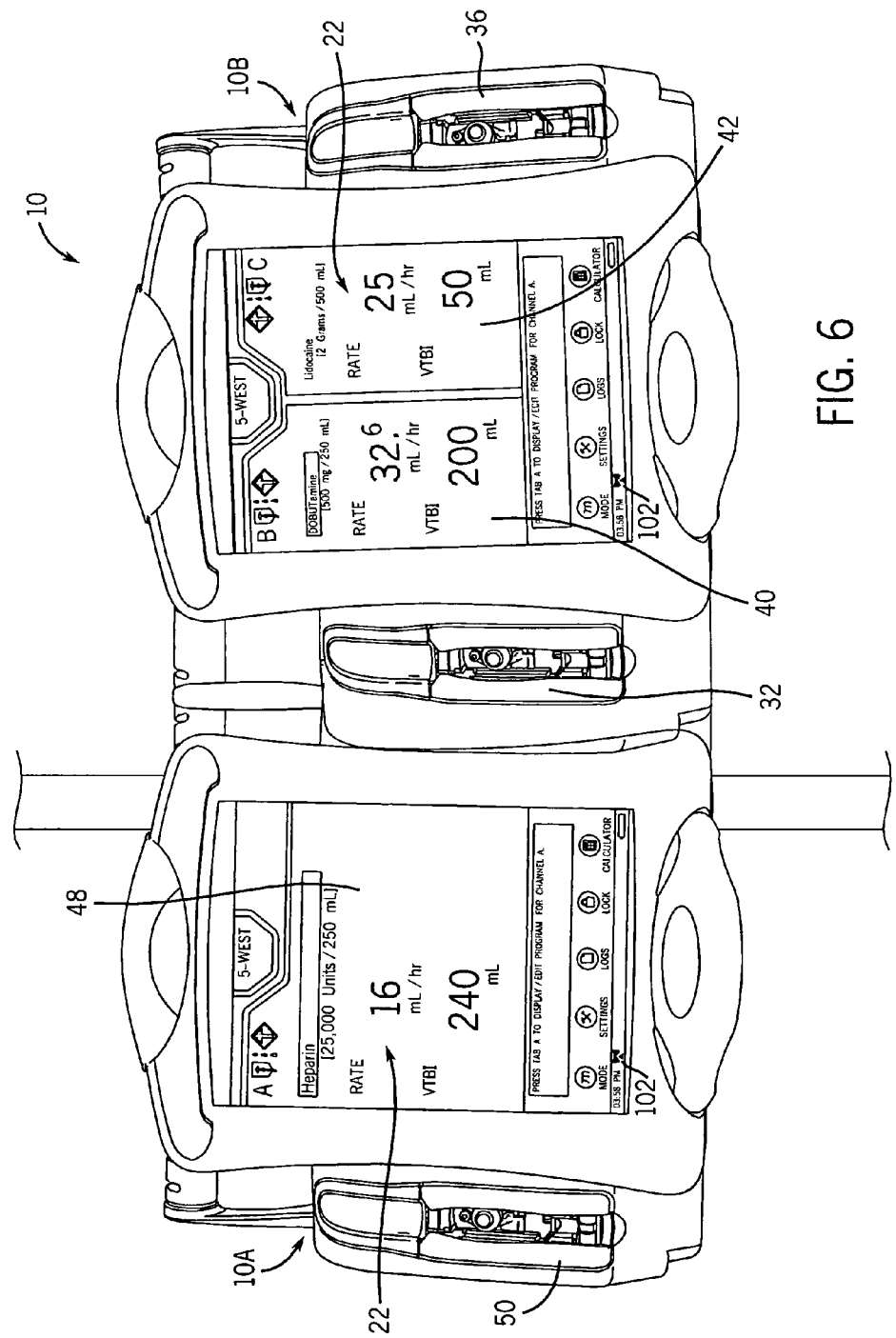
FIG. 6 is a front view of two medical devices associated with one another and having displays according to the present invention.

With reference to FIGS. 2-6A, medication errors often result from human errors in programming the medical device 10. Reducing steps that require manual comprehension, making the programming sequence more intuitive and eliminating labor-intensive tasks minimizes such errors. In multi-channel pumps 10B (FIG. 2) it has heretofore been difficult to associate the channel with its fluid container, tubing and infusion site during programming. This problem is compounded if there are a series of standalone medical devices 10 connected for operation in a coordinated manner, such as in sequence or in unison. For example, FIG. 3 shows two single channel pumps 10AR and 10AL connected wirelessly, while FIG. 6 shows a single channel pump 10A and a multi-channel pump 10B physically connected for operation in a coordinated manner. Since a user is able to select a channel through a physical association with the desired channel in the present invention, the task is more intuitive and less labor demanding than manually entering channel letter or number information through a keypad on the touch screen 22.

With reference to FIG. 1, the present invention provides a machine-readable input device 30 that addresses the problem of correctly performing a channel association when programming the medical device 10. The machine-readable input device 30 communicates with the medical device 10 to input machine-readable information to the medical device 10. The machine-readable input device 30 can communicate, directly or indirectly, with the medical device 10 via a wireless or hard-wired connection. The machine-readable input device 30 can be a device that is separate from but associated or in communication with the medical device 10.

The machine-readable input device 30 can be any sort of data input means, including those adapted to read machine-readable indicia, such as a barcode scanner or handheld personal digital assistant (PDA). Alternatively, the machine-readable input device 30 may be operable to read in other known forms of machine-readable information, such as radio frequency identification tags (RFID), touch memory, digital photography, biometrics, etc. For example, the device 30 can be a digital camera capable of generating an electronic image. In addition to assisting in channel association, such a device is useful for forming an electronic image of all or some portion of a drug container label, as will be discussed later.

Figure 2:
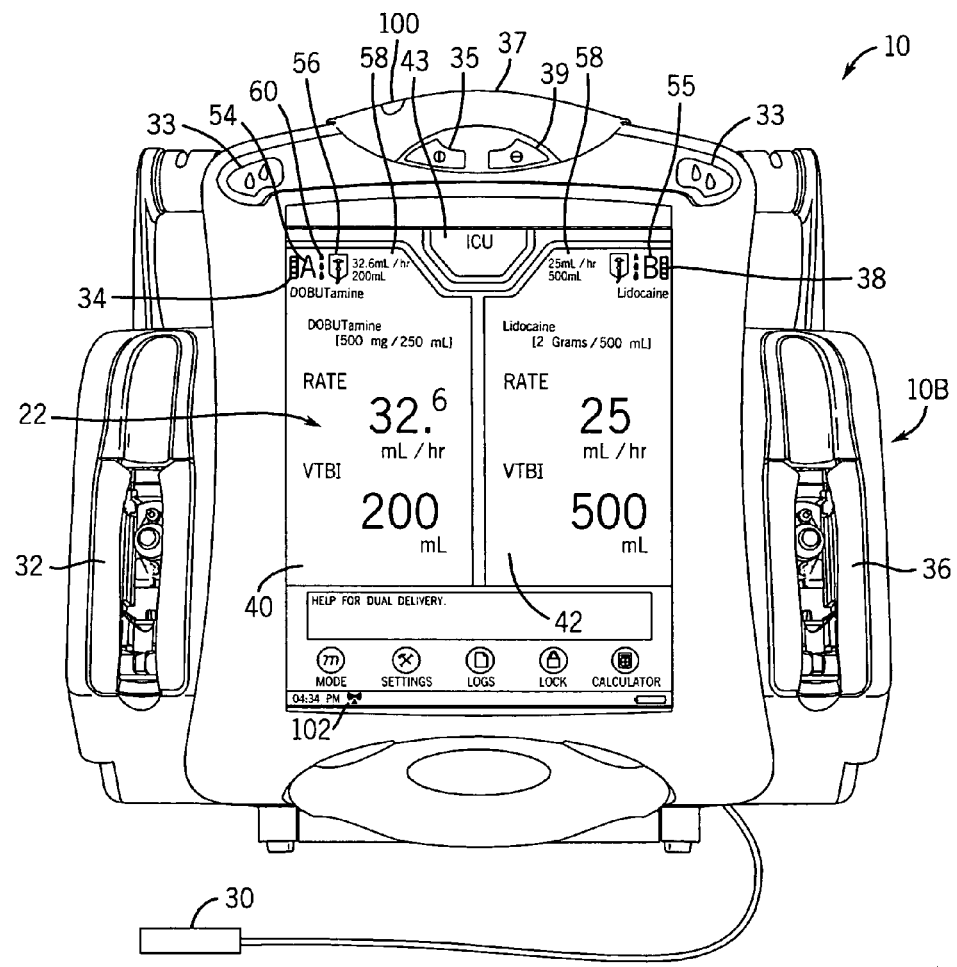
FIG. 2 is perspective view of a multi-channel medical device in communication with a machine-readable input device according to the present invention and shows a split screen display, having one portion associated with each channel, which is adapted to be displayed and viewed from afar during normal delivery of fluid.

With reference to FIG. 2, the medical device 10 is a multi-channel pump 10B having a first channel 32 with first channel machine-readable label 34 and a second channel 36 with a second channel machine-readable label 38. A user of the medical device 10 operates the machine-readable input device 30 to select a channel from one or more channels 32 and 36, by scanning in the associated machine-readable label 34 or 38.

The user selects the desired channel 32 or 36 by using the machine-readable input device 30 to scan a factory or hospital programmed, unique, machine-readable label 34 or 38 that is electronically generated and presented on the screen 22, preferably juxtapositioned near the respective channel 32 or 36. Alternatively, the machine-readable labels 34 and 38 are physically affixed to the medical device 10, preferably on or juxtapositioned near the channel 32 and 36, respectively. Since the machine-readable labels 34 and 38 are generated and/or can be stored in memory 24 by the pump 10B, the pump 10B can associate the machine-readable labels 34 and 38 to the channels 32 or 36. The pump 10B then allows the user to program and activate the selected channel 32 or 36. The user may also manually select the desired channel by touching an appropriate folder tab on the touch screen. The folder tabs are labeled and/or physically arranged on the screen so as to be proximate to the corresponding channel 32 or 36. That is, the "A" tab is juxtapositioned near or adjacent to the "A" channel 32 and the "B" tab is juxtapositioned near or adjacent to the "B" channel 36.

With reference to FIG. 3, two single channel pumps 10AL and 10AR are wirelessly connected. Together, the pumps 10AL and 10AR collectively have first channel 32 with first channel machine-readable label 34 and "second" channel 36 with "second" channel machine-readable label 38. A user of the single channel pump 10AR operates the machine-readable input device 30 to select a channel 32 or 36 by scanning in the associated machine-readable label 34 or 38 with the machine-readable input device 30. Thus, by using the machine-readable input device 30, the user can select a channel from more than one channel 32 and 36 of a multi-channel pump 10B or from any collection of pumps 10AR, 10AL (FIG. 3) or 10A and 10B (FIG. 6) connected to one another physically or wirelessly. Of course, the channel can alternatively be selected by touching the appropriate channel screen portion, indicator or folder tab on the screen 22.

In a further aspect of the wireless embodiment, all the medical devices can periodically broadcast a unique wireless device/channel IP address and/or a self-generated unique machine-readable label (for example, a barcode) 34 or 38 that can also be presented on the screen 22. Alternatively, the machine-readable labels 34 and 38 are physically affixed to or posted on the medical device 10. Each medical device will correlate such broadcasted or posted device/channel IP addresses and/or barcodes with a particular patient, who is also identified by a unique machine readable label (not shown) or patient IP address. The user associates the desired pump(s) or channel(s) 32, 36 with the patient by using the machine-readable input device 30 to scan the unique machine-readable labels 34, 38 and the patient's machine readable label. This causes the appropriate pump processor(s) 18 to associate the appropriate pump channel(s) 32, 36 with the patient. Then the pumps or channels can associate, communicate, and coordinate with each other wirelessly.

Alternatively, one of the pumps equipped with a machine readable label reader 30 can associate with other pumps irrespective of the patient by reading or receiving the IP address or machine readable label information. When the channel machine-readable label 34 or 38 of one pump 10AR or 10AL is read in by the machine-readable input device 30 associated with the other pump 10AL or 10AR, the first pump 10AL or 10AR can associate the read machine-readable label 34 or 38 to the IP address to facilitate subsequent wireless communication, coordination and association of the medical devices 10AR, 10AL.

With reference to FIGS. 1 and 2, the graphical user interface program 26 reallocates screen 22 for a medical device 10. Specifically, FIG. 2 illustrates a multi-channel infusion pump 10B with a split touch screen 22 having a first channel screen portion 40 associated with first channel 32 and a second channel screen portion 42 associated with the second channel 36. Each channel screen portion 40 and 42 presents a subset of the delivery information regarding the respective channels 32 or 36, including without limitation therapeutic agent name, concentration, dose rate, VTBI, and alarm information, in a font size at least twenty-eight points so that it is easily readable by a user from approximately fifteen to twenty feet (4.6-6.2 meters) away. This is what is referred to as a "far view" delivery screen. Similarly, FIG. 5 illustrates a far view delivery screen for a single channel pump 10A (FIG. 6). The far view delivery screens of FIGS. 2 and 5 display subsets of the information found on the relevant "near view" delivery screens of FIGS. 2A and 5A.

Figure 2A:
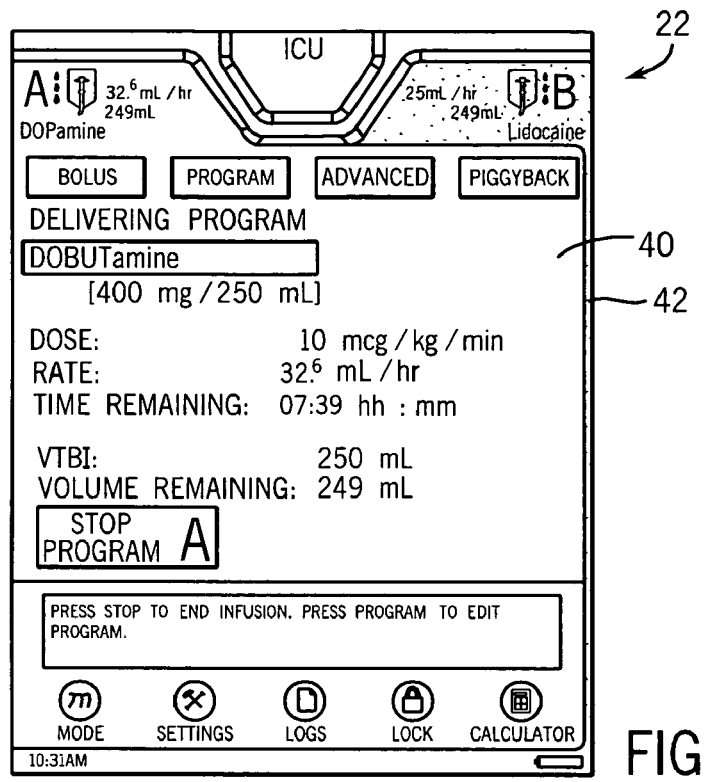
FIG. 2A a screen display of the multi-channel medical device of FIG. 2 that is adapted to be displayed and viewed up close during normal delivery of fluid through channel A according to the present invention.
Figure 5A:
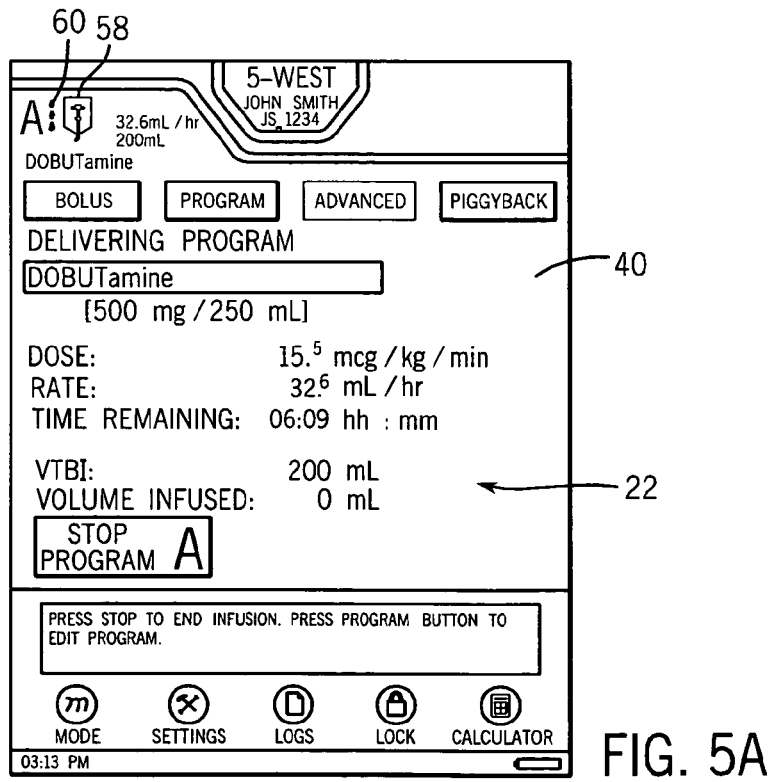
FIG. 5A is a screen shot of a single channel medical device with a screen display that is adapted to be displayed and viewed up close during normal delivery of fluid.

Upon a user touching one of the tabs "A" or "B" or anywhere on the channel screen portions 40 or 42 of the far view delivery screen, a "near view" delivery screen is presented on the screen 22, as best seen in FIG. 2A or 5A. The channel screen portion 40 or 42 selected or corresponding to the tab selected expands in area but the size of at least some of the text therein is shrunk. The font size for rate and VTBI information on the near view delivery screen is substantially less than twenty-eight points. The other channel screen portion 40 or 42 (if present) is shrunk, hidden or moved to the background to limit its space on the screen 22. Preferably, if the "A" tab or the first channel screen portion 40 is selected, the "B" tab of the second channel screen portion 42 remains exposed but is grayed or colored differently to indicate it is not the channel of interest. Thus, the second channel screen portion 42 becomes smaller than the first channel screen portion 40, as the first channel screen portion 40 is currently being viewed and adjusted by the user and is therefore of primary concern. The second or B channel can be selected in a similar manner, whereupon the first channel portion 40 of the screen 22 will become smaller and the second channel portion 42 will become larger. Since the screens for the respective channels are substantially identical, except for the position of their tabs 58, features shown in the drawings and described below relative to the A channel also apply to the B channel, and vice versa.

Figure 2B:
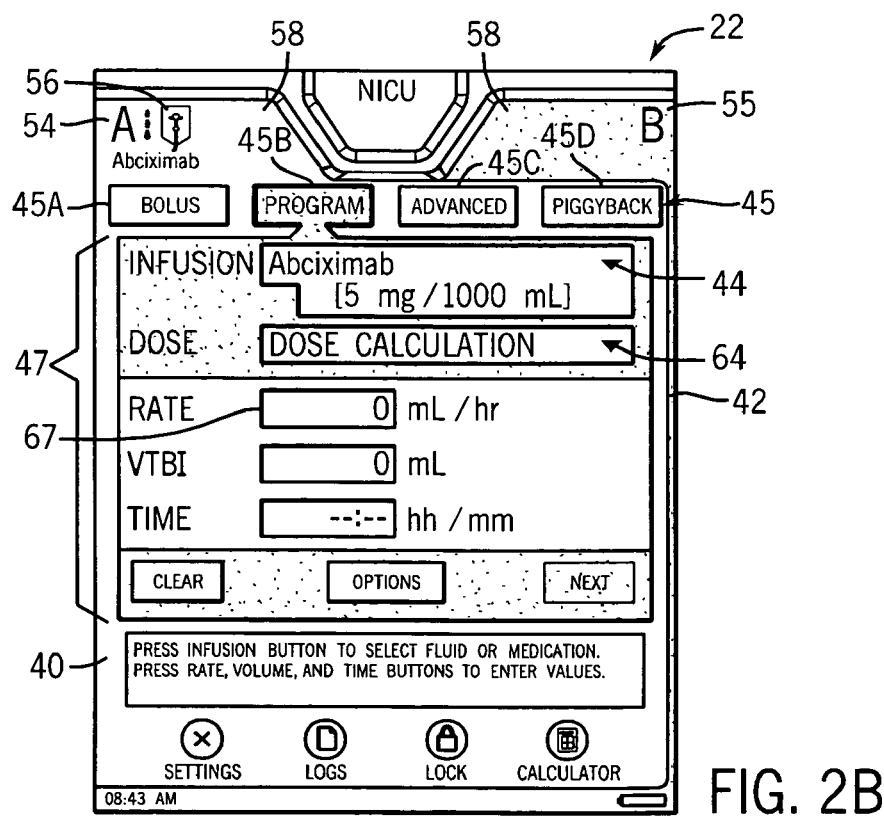
FIG. 2B is a screen display of the multi-channel medical device of FIG. 2 that is adapted to be displayed and viewed up close during programming of fluid delivery according to the present invention. The display is rearranged to maximize the information presented for the channel being adjusted, minimize the information presented for the channel not being adjusted, and provide additional display space for data entry fields.

As best understood in view of FIGS. 2A and 2B, the shrinkage of one of the channel screen portions 40 and 42 and enlargement of its counterpart also provides additional space for one or more data display or data entry fields to be placed on screen 22. As discussed below, data displays or data entry fields are placed on screen 22 in space previously occupied by portions of the channel screen portion 40 or 42. This reallocation of space on screen 22 permits the user to enter inputs more easily since the data entry field can be large, preferably at least as large or, more preferably, larger in area than the original channel screen portions 40 and 42 were in the delivery screen mode. Additionally, the reallocation of space on screen 22 provides greater space for presenting information on the channel being adjusted or monitored, in this case the first channel 32.

With reference to FIGS. 2A, 2B, and 5B-5L, to program the device 10, the user presses the touch screen 22 in the tab area A or B to select the channel. Of course, this step is unnecessary in the case of a single channel pump. The screen display presents the basic "programming" screen 22 shown in FIG. 2B or 5E. When the user selects an infusion by touching the down arrow 44 or area 134, a drop down menu or list of selectable items (in this case a drug library of therapeutic agents) appears or "explodes" as a pop up screen 46, as illustrated in FIG. 5F.

Figure 5B:
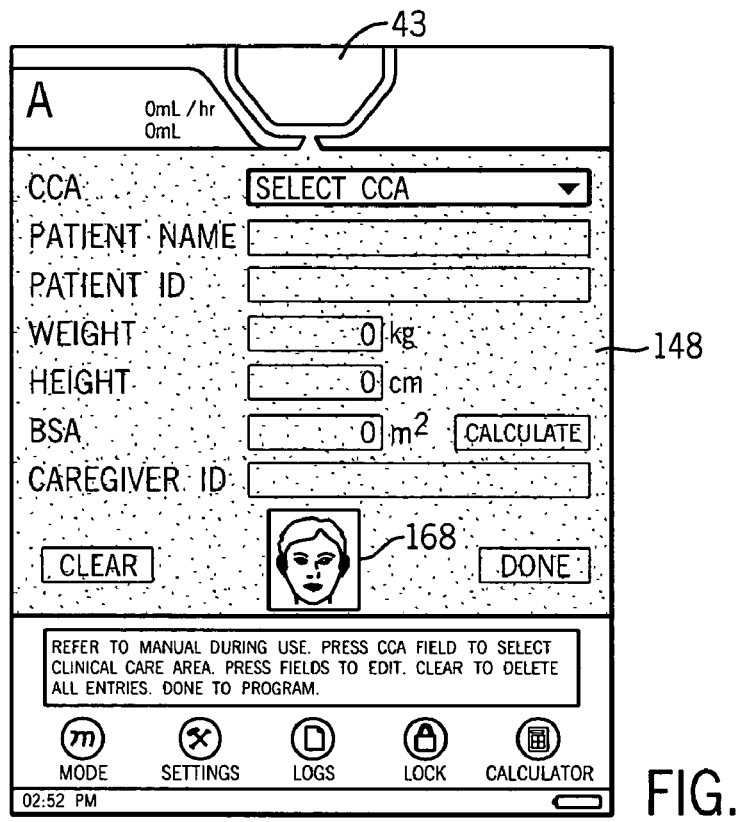
FIGS. 5B-5N and 5P-5Z provide screen shots of the display of a single channel medical device during programming and show additional features of the present invention.
Figure 5C:
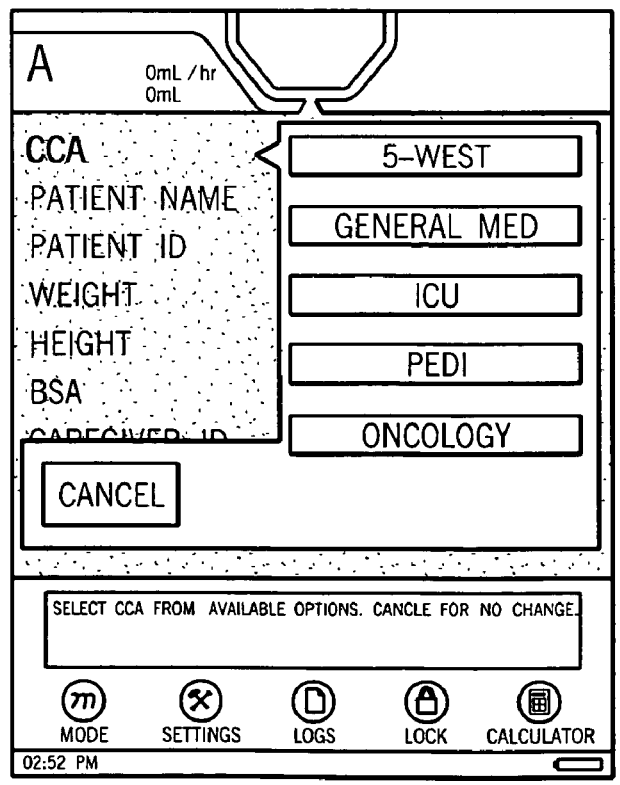
Figure 5D:
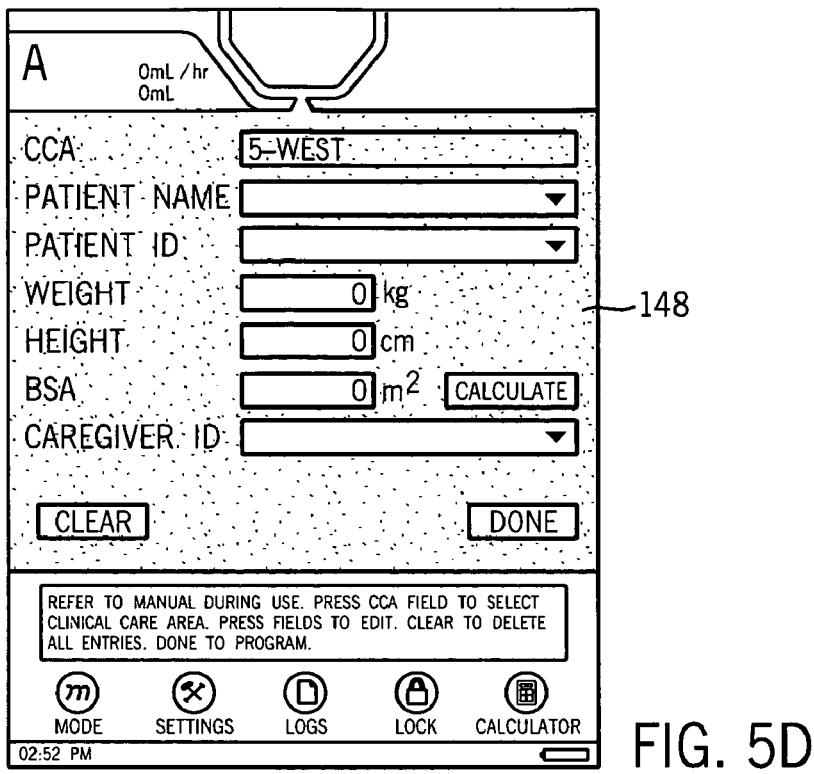
Figure 5E:
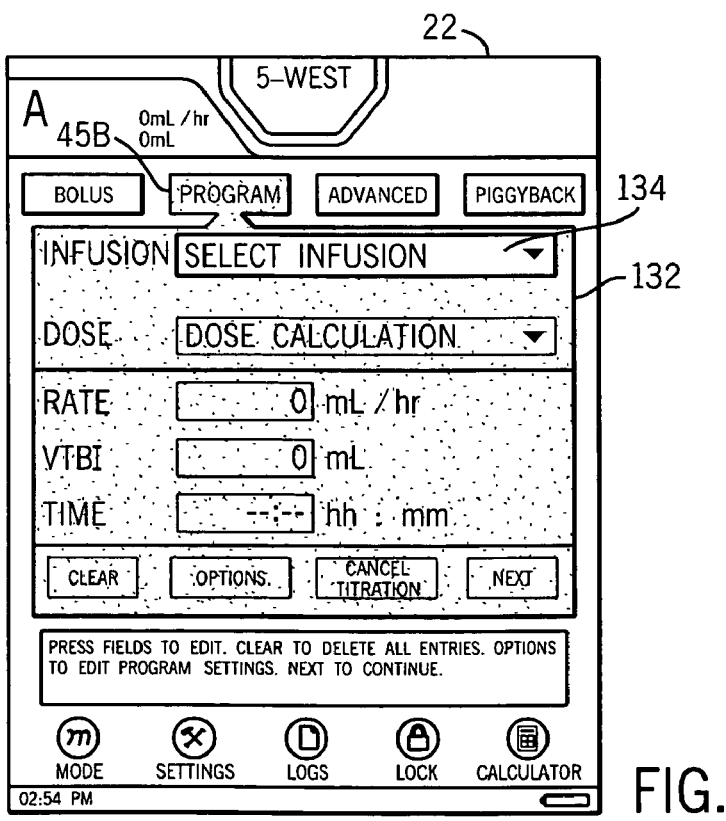
Figure 5F:
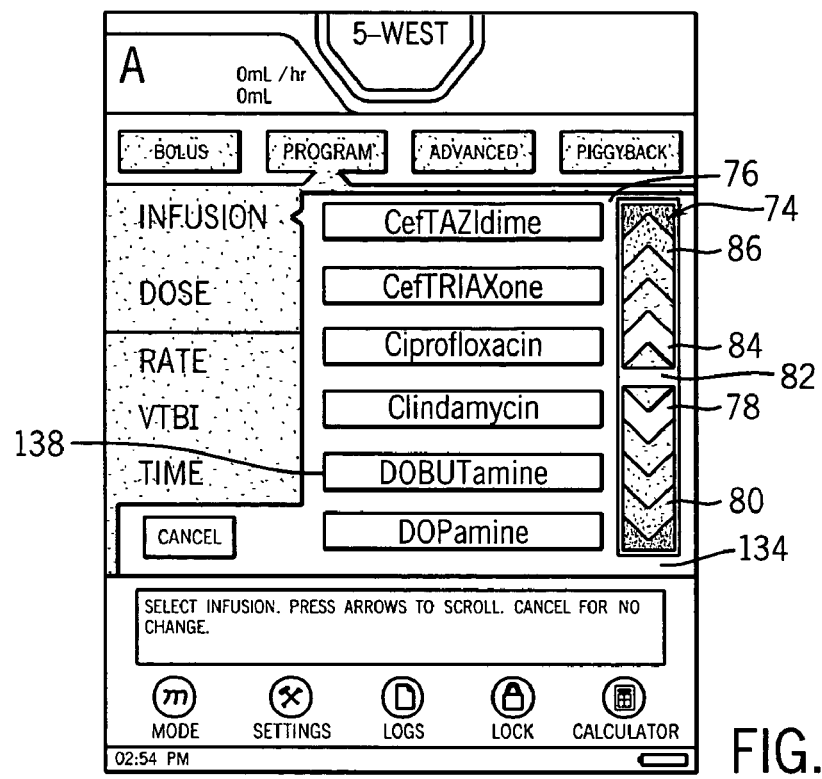
Figure 5G:
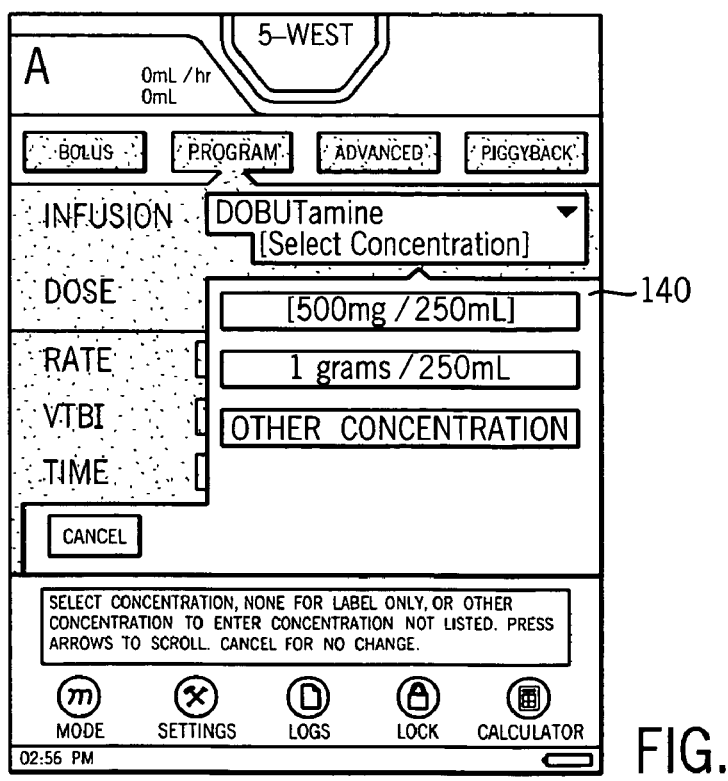
Figure 5H:
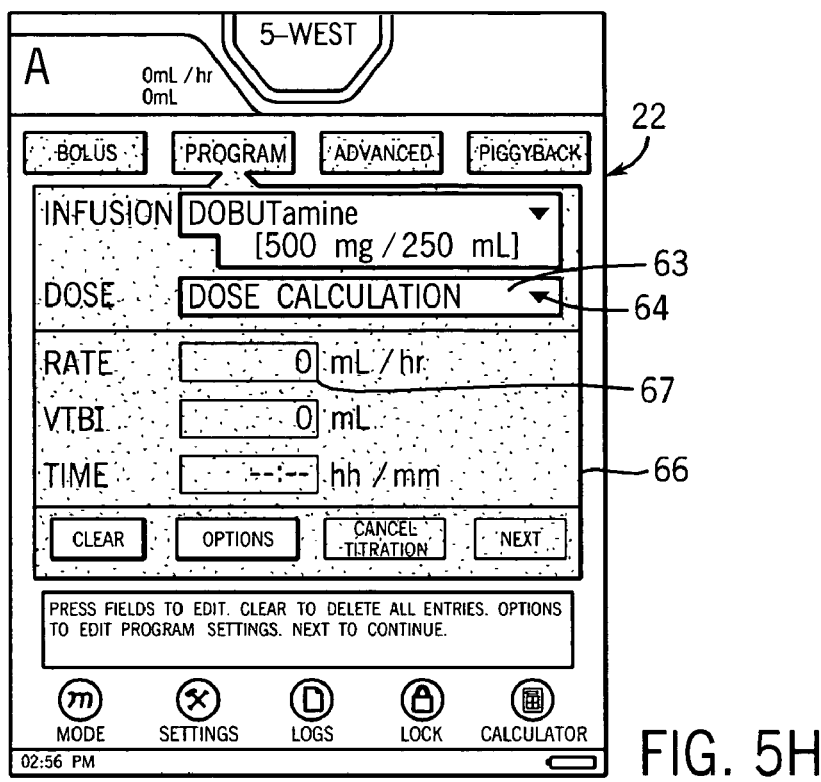

With reference to FIGS. 2B and 5H, when the user touches the Dose Calculation area 63 or the down arrow or explode button 64 adjacent the words Dose Calculation, the space on the screen 22 is reallocated to provide a dose calculation field 66 where the rate can be calculated based on a desired dose for the patient's weight, height or body surface area (BSA). Alternatively, the rate can be entered directly in the rate calculation field 67 shown in FIG. 2B.

Figure 5I:
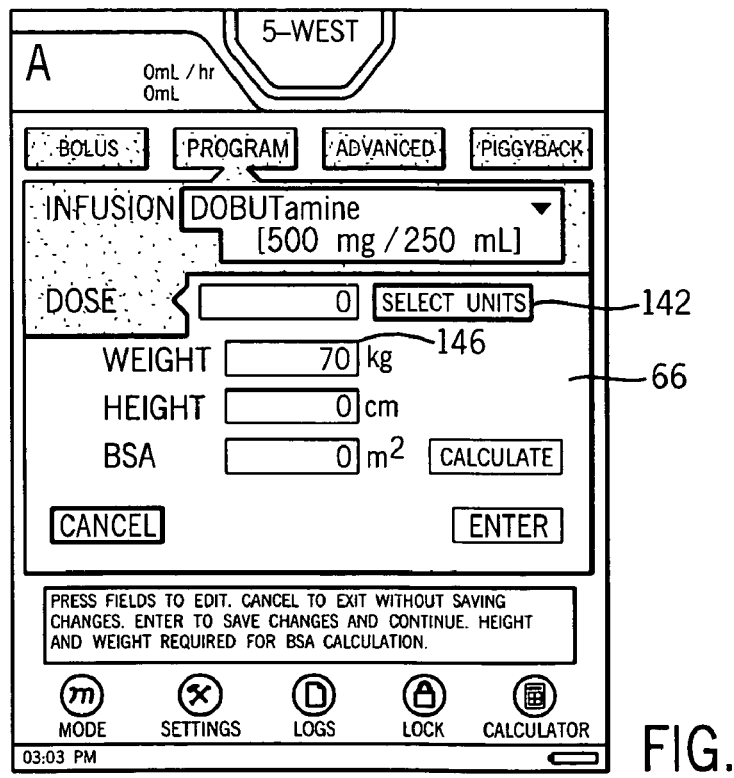
Figure 5J:
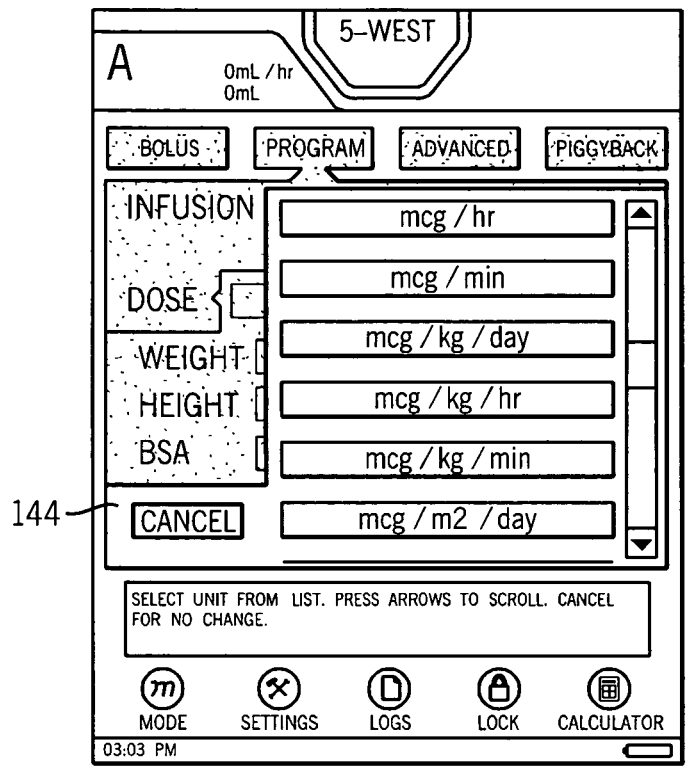
Figure 5K:
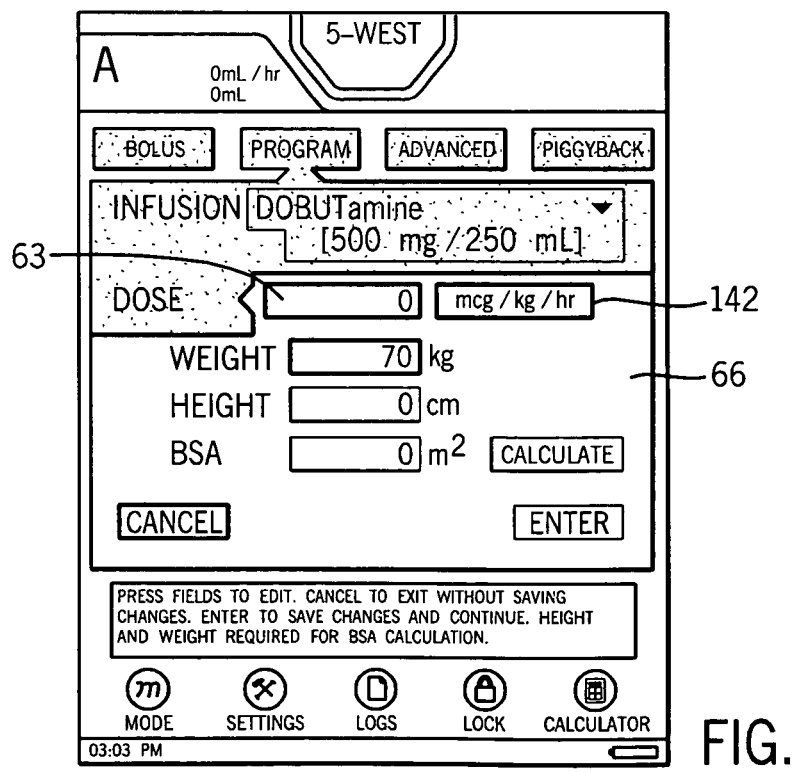
Figure 5L:
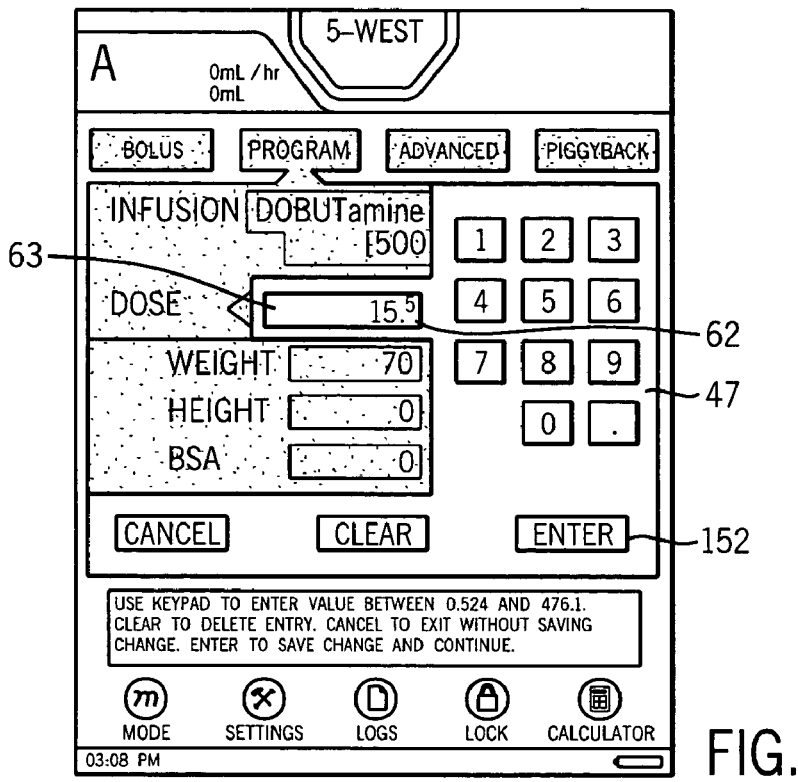

When any of the fields for Weight, Height, BSA, Rate, VTBI or Time is selected, a keypad data entry field 47 is placed on screen 22 in space previously occupied by portions of the channel screen portion 40 or 42, as illustrated in FIG. 5L. This reallocation of space on screen 22 permits the user to enter inputs more easily since the data entry field 47 can be large, preferably at least as large or, more preferably, larger in area than the original dose and rate calculation fields or the original channel screen portions 40 and 42 in the delivery screen mode.

Figure 7:
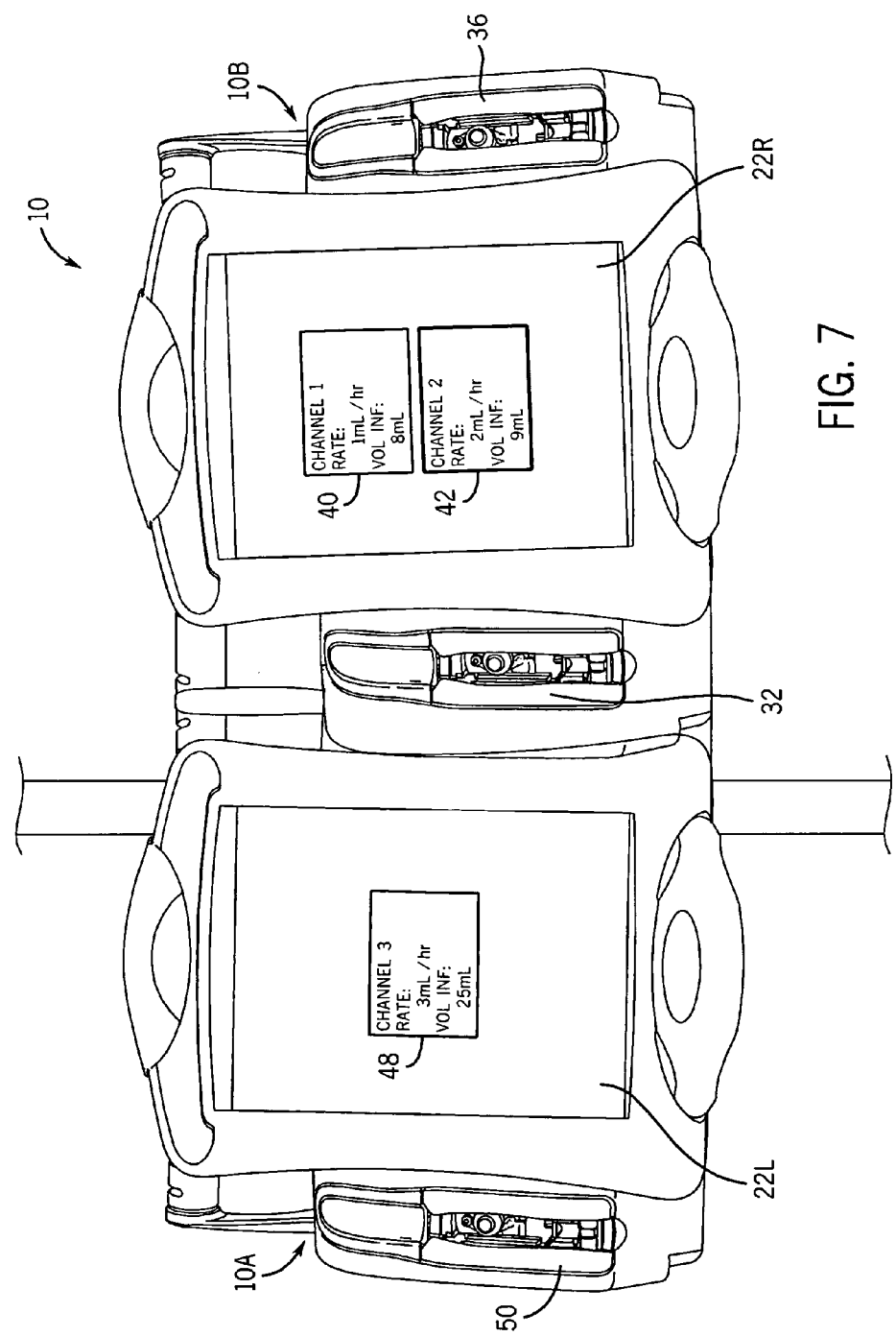
FIG. 7 is a front view of the two medical devices of FIG. 6, which shows an alternative embodiment of the screen displays according to the present invention.
Figure 8:
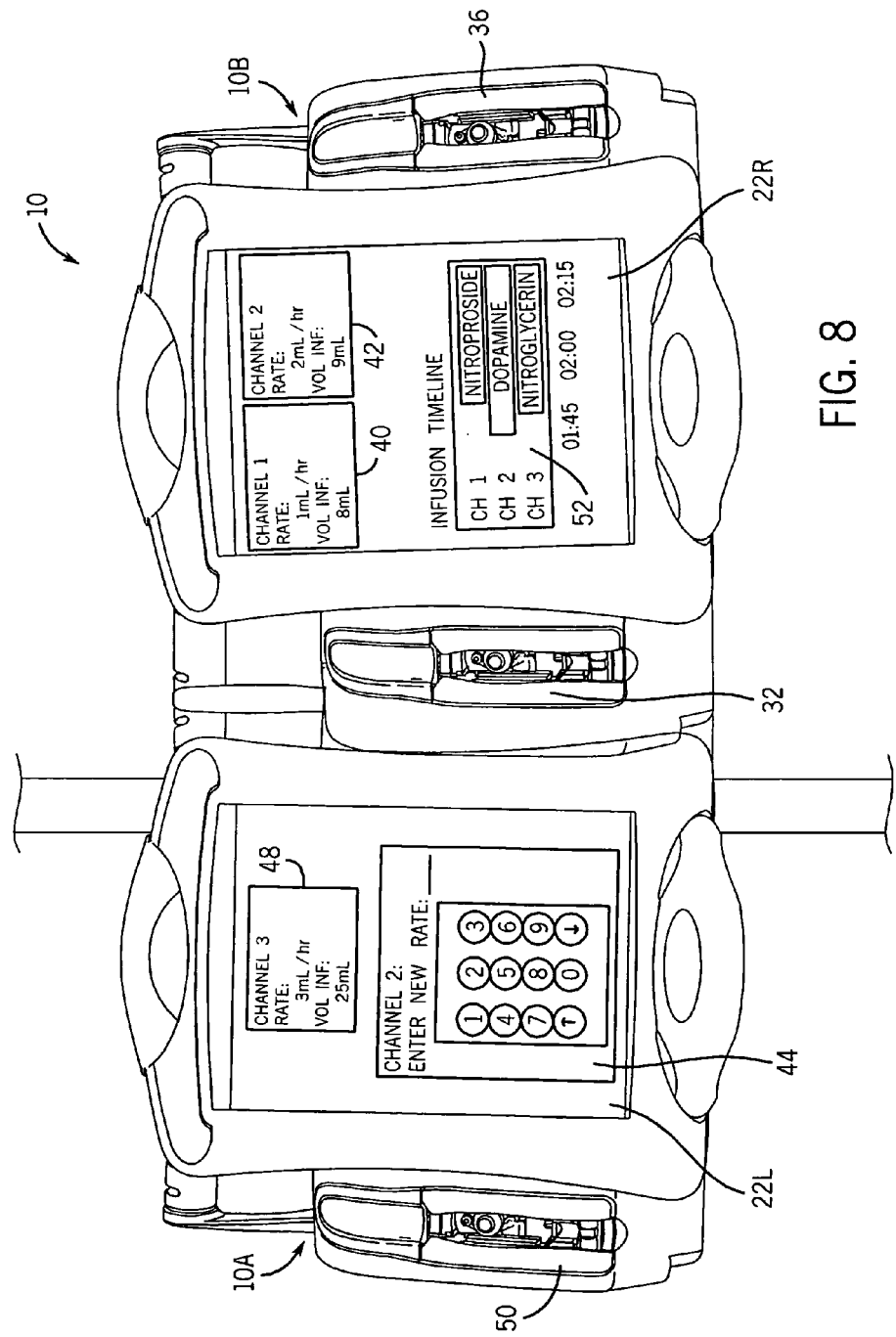
FIG. 8 is a front view of the two medical devices of FIG. 6, which shows an alternative embodiment of the screen displays wherein the channel status information is collapsed on the display of the medical devices, additional operational information of the event time line for all channels is presented on one of the medical devices, and the other medical device presents a data entry field used for programming of either medical device.

With reference to FIGS. 7 and 8, in an alternative embodiment, the graphical user interface 26 reallocates and combines two or more displays 22 (22L and 22R) in a different manner upon associating two or more medical devices 10 with one another. As shown, a single channel medical device 10A is associated with a multi-channel medical device 10B. This is for illustrative purposes only, and other various combinations of multiple medical devices 10 may be made without departing from the present invention. Additionally, while the medical devices 10A and 10B are shown as being physically associated, it is contemplated that they may alternatively be wirelessly associated (as illustrated in FIG. 3 and discussed in more detail above).

With reference to FIG. 7, the touch screen 22L of the single channel medical device 10A has a third channel screen portion 48 associated with its channel 50. The third channel screen portion 48 presents the programming and delivery information of the third channel 50, including but not limited to rate and volume information. Upon the association of the medical devices 10A and 10B, the third channel screen portion 48 presents an indication that the medical device 10A contains its own A channel (channel 3).

Figure 7A:
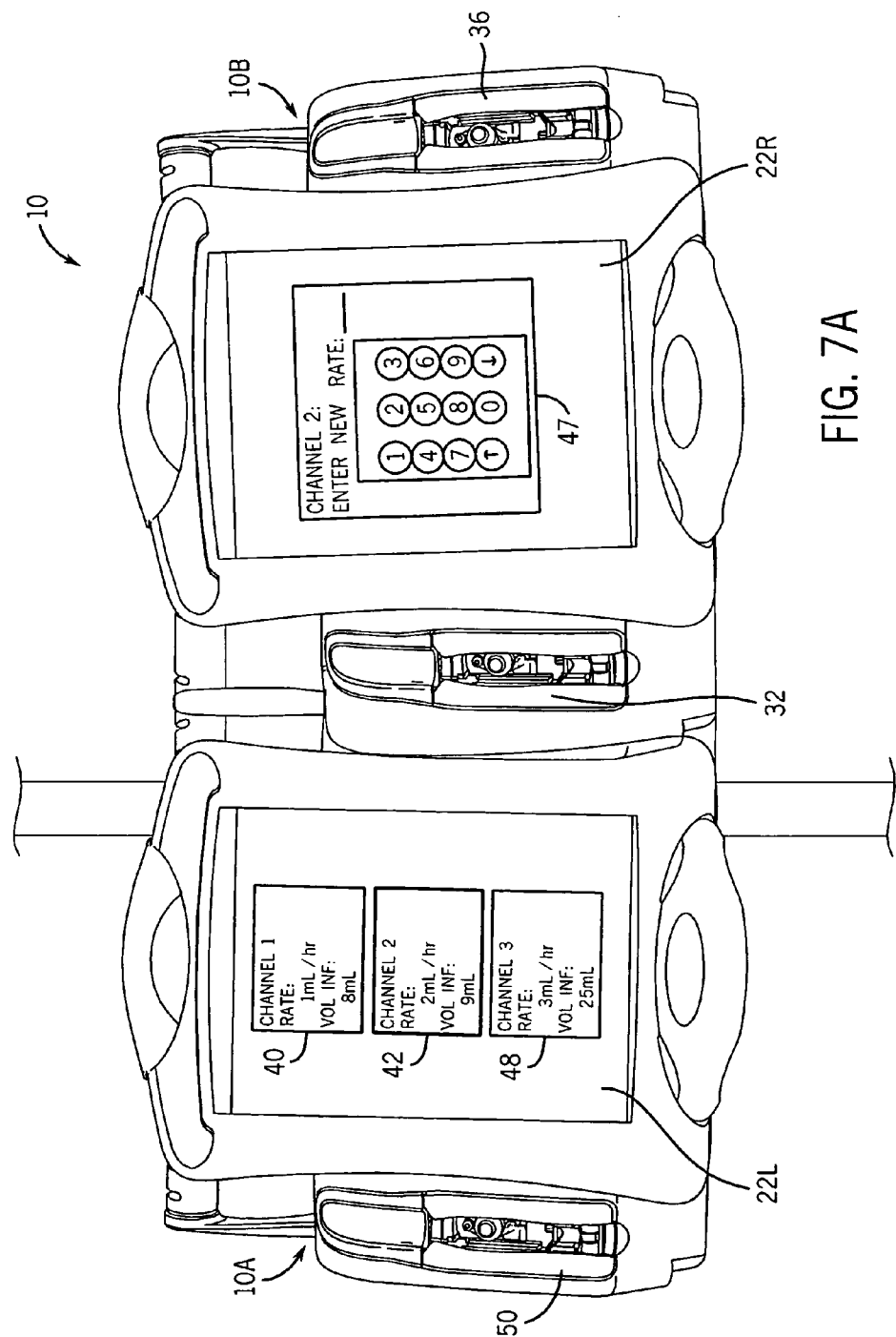
FIG. 7A is a front view of two medical devices similar to FIG. 7 but shows the channel status information collapsed onto the display of one of the medical devices and the other medical device presents a data entry field used for programming one of the channels.

With reference to FIG. 7A, upon a user request for programming or changing the rate in the second channel 36, the infusion information is re-arranged on the displays 22L and 22R. As seen, the channel screen portions 40, 42, and 48 are shrunk to limit their space and distributed on the screen 22L. The keypad data entry field 47 is placed on screen 22R in the space previously occupied by portions of each channel screen portion 40 and 42. This reallocation of space on displays 22L and 22R permits the user to enter inputs more easily since the data entry field 42 is dimensionally larger than the channel screen portions 40, 42 and 48. This reallocation of space on screen 22 permits the user to enter inputs more easily since the data entry field 47 can be large, preferably at least as large or, more preferably, larger in area than the original channel screen portions 40 and 42 were in the delivery screen mode.

With reference to FIG. 8, upon a user request for operational information for the medical devices 10A and 10B, the infusion information is re-arranged on the displays 22L and 22R to make room for an operational information display of the requested operational information. The operational information display 52, for instance, is a representation of the infusion timeline for each channel 32, 36, and 50. Alternatively, the operational information 52 includes information collected from all the medical devices 10A and 10B associated together, including but not limited to pump status, error messages, and other information. As seen, each channel screen portion 40, 42, and 48 is shrunk to limit their space on the respective displays 22L and 22R. The keypad data entry field 44 is placed on screen 22L in the space previously occupied by a portion of the third channel screen portion 48. Likewise, operational information display 52 is placed on screen 22R in the space previously occupied by portions of the first and second channel screen portions 40 and 42. This reallocation of space on displays 22L and 22R permits the user to enter inputs more easily in the data entry field 47, and permits concurrent presentment of additional operational information. The operational information can thus all be centralized and presented in one screen or dispersed according to the needs of the user.

With reference to FIGS. 1 and 2, the graphical user interface 26 provides channel indicators presented on screen 22. The channel indicators associate on-screen programming, delivery, and alarm information with a particular delivery channel by using graphical depictions such as a channel indication icon 54, 55 and an infusion status icon 56. The channel indication icon 54 or 55 is a graphical item clearly associating on-screen programming, delivery, and alarm information with a specified associated delivery channel. The channel indication icon 54 or 55 may include but is not limited to a user readable letter or number, a machine-readable indicator 34, or a combination thereof.

Figure 9:
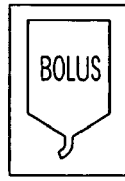
FIG. 9 is an illustration of a number of infusion status icons according to the present invention.
Figure 9:
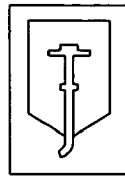
Figure 9:
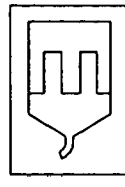
Figure 9:
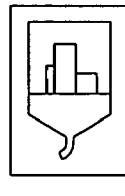
Figure 9:
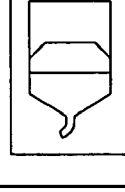
Figure 9:
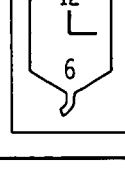
Figure 9:
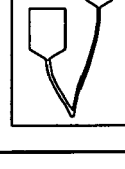

With reference to FIGS. 2 and 9, the infusion status icon 56 is a graphical item indicating the type of delivery program being delivered by the medical device. The infusion status icon 56 is provided by a bag icon that depicts the current program. As shown, multiple delivery options are provided with their own distinct infusion status icon 56 as follows: bolus infusion status icon 56A, basic program infusion icon 56B (constant delivery rate), intermittent therapy icon 56C, multi-step therapy icon 56D, taper therapy icon 56E, variable time therapy icon 56F, and piggyback infusion status icon 56G.

With reference to FIG. 2, the channel indicators 54 and 55 are located on a tab 58 associated with a specified delivery channel of the medical device. The placement of channel indicators 54 and 55 on tab 58 provides a clear and strong visual association between programming, delivery, and alarm information and the specified associated delivery channel. The indicator 54 and its tab 58 are right justified and the indicator 55 and its tab 58 are left justified on the display screen 22.

With reference to FIGS. 1 and 5A, the graphical user interface program 26 provides a drip indicator icon 60 presented on screen 22. The drip indicator icon 60 provides a series of vertically aligned "raindrop shapes" of progressively increasing size which are animated by being illuminated sequentially from top to bottom when a delivery is occurring. The drip indicator icon 60 is located on a tab 58 associated with a specified delivery channel of the medical device 10. Alternatively, the drip indicator 60 can be a single raindrop shape moving downwardly on the tab 58. Alternatively, a drip indicator 60A can be provided remote from the display screen 22 on the device.

Figure 5M:
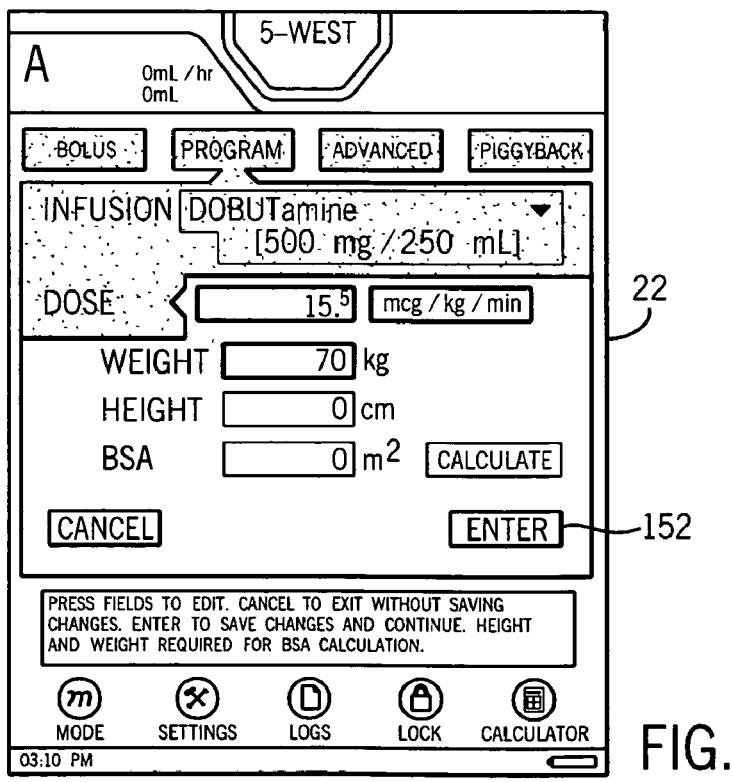
Figure 5N:
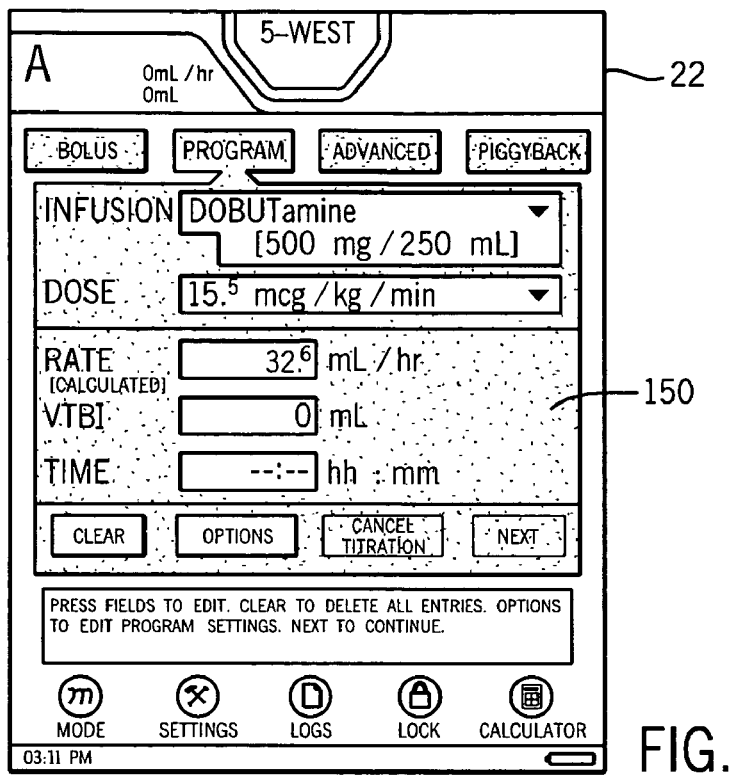
Figure 5P:
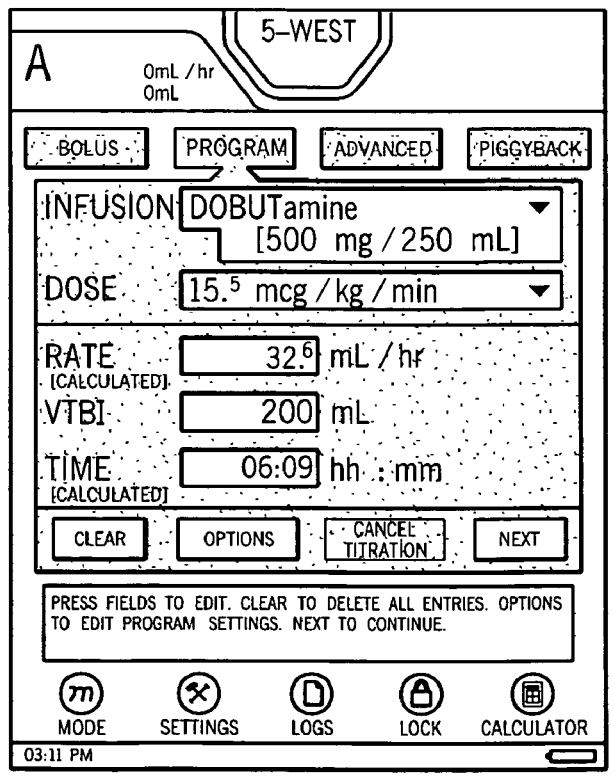
Figure 5Q:
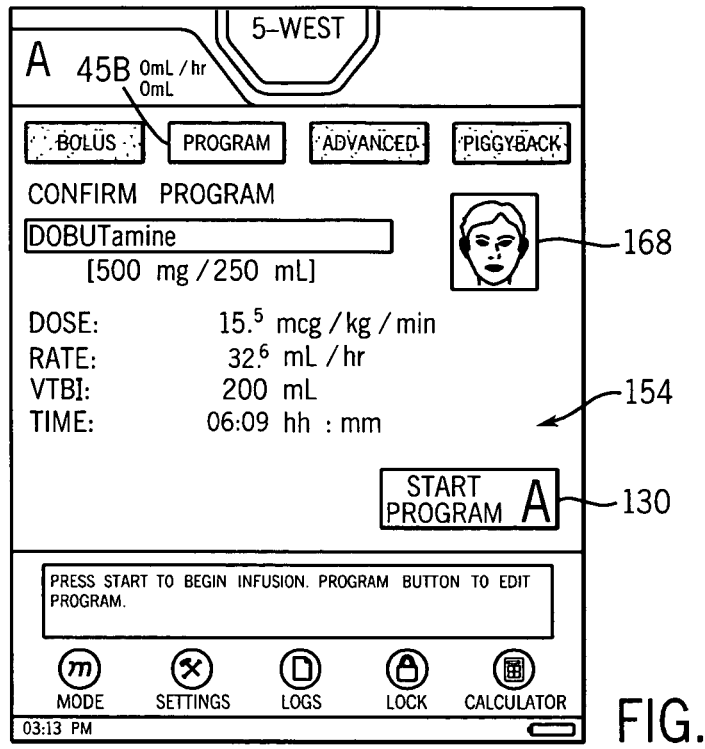

With reference to FIGS. 1, 5B and 5Q, the graphical user interface 26 provides a rendering, digital photograph or other indicia 168 identifying the patient that is presented on the screen 22. Such a photograph 168 of the patient's face allows a user of the medical device 10 to confirm that the medical device 10 is serving the correct patient. The patient photograph 168 provides an additional or alternative validation of the "right patient" prior to delivery, which can be accomplished by caregiver visual confirmation of the patient. Additionally, the use of the patient photograph 168 on the medical device 10 is advantageous, as it is often undesirable due to privacy concerns to present the patient's name for identification purposes, and other means such as unique identification numbers are sometimes cumbersome for a user.

The patient rendering 168 is a picture, sketch, or other graphical representation of the patient's face. For example, a photograph of the patient can be taken with a digital camera (not shown) upon admission to the hospital and the digital photo is transmitted to the medical device 10. The image 168 of the patient is sent to the screen 22 of the medical device 10. The patient rendering 168 is then placed on the screen 22 and the caregiver confirms a patient match upon visual comparison of the patient with the patient rendering on the screen 22.

With reference to FIGS. 1 and 5L, the graphical user interface 26 provides a vertically offset decimal number 62 on screen 22. The vertically offset decimal number 62 presents decimal numbers in a raised or lowered decimal format. The digits presented to the left of the decimal point are of a given height. The digits to the right of the decimal point are of smaller height, with their bottom in this example raised from bottom of the digits to the left of the decimal.

For example, the digits presented to the left of the decimal point are standard font size and standard placement, while the digits presented to the right of the decimal point are ¾ height and aligned at their bottom approximately with the middle of the digits to the left of the decimal. The raised decimal number 62 focuses the user's attention to the fact that a presented or entered number includes digits to the right of the decimal point. This is a useful means of reducing user errors related to numbers with decimals. The format of the raised decimal number 62 can be used in any data entry fields and data display fields that allow for numbers with decimals. Of course, the digits to the right of the decimal can also be lowered with respect to the digits to the left of the decimal point in a similar manner to achieve similar results.

With reference to FIGS. 1, 5H and 5I, the graphical user interface 26 provides an "explode" button 64 on screen 22. The explode button 64 provides access to a data entry field 66. The explode button 64 is shown in its non-activated dormant state in FIG. 5H. When the explode button 64 is activated, the explode button 64 expands to a larger area, as shown in FIG. 5I. The activated explode button 64 provides access to a data entry field 66 that was previously not accessible in FIG. 5H.

Figure 15:
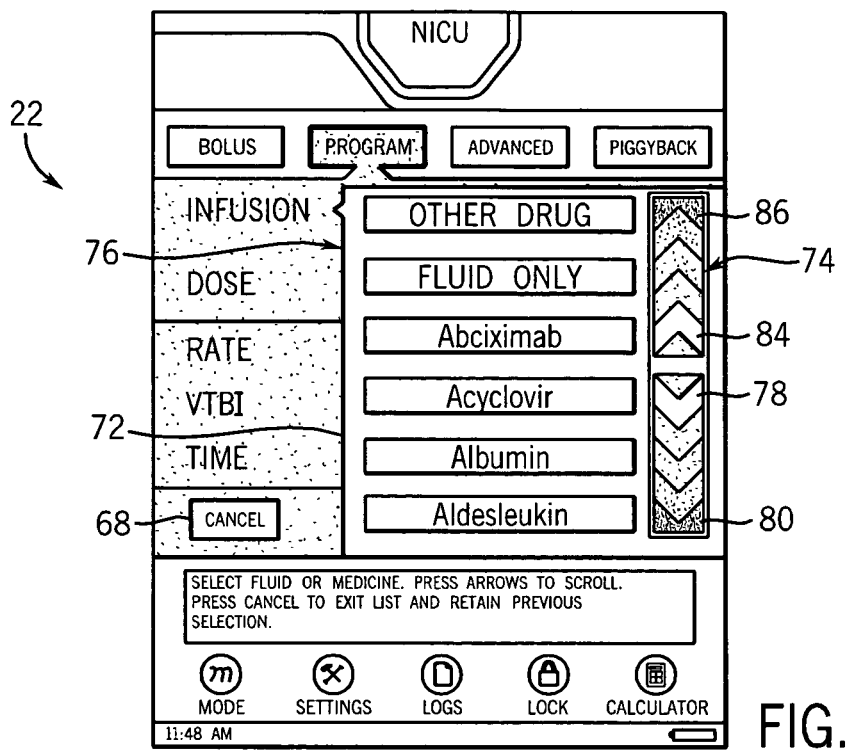
FIGS. 15-17 are screen shots of the medical device illustrating a dual function clear/cancel button feature.
Figure 16:
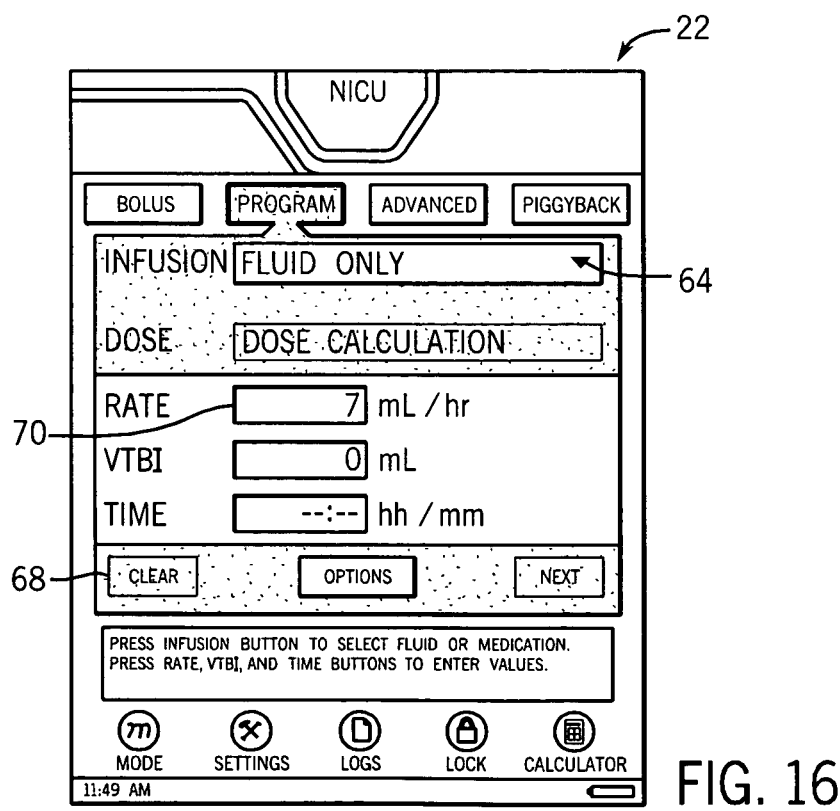

With reference to FIGS. 1 and 15-17, the graphical user interface 26 provides a dual function clear/cancel button 68 on screen 22. The dual function clear/cancel button 68 provides in a single button area the functions of clearing user entered content or keyed-in values and canceling a currently selected programming operation or screen display to return to the previous state or screen display. The interface 26 requires a predetermined delay before the user is presented with the opportunity to initiate the clear function after initiating the canceling function. The delay helps avoid inadvertently clearing some or all entered parameters, yet allows a common button area to be used. In operation, the dual function clear/cancel button 68 normally presents a visual indication of a selectable cancel function, as shown in FIG. 15, unless a user entered or keyed-in data entry field is displayed. For the black and white FIGS. 15-17, the button 68 shows its status by having a white background outlined with bold black lines if selectable or operational and by having a stippled background outlined in normal weight black lines if nonselectable or nonoperational. One skilled in the art will appreciate that the color touch screen 22 of the present invention can provide other visual indications of the status of button 68, including but not limited to various colors, hues, shading, and outlining.

Figure 17:
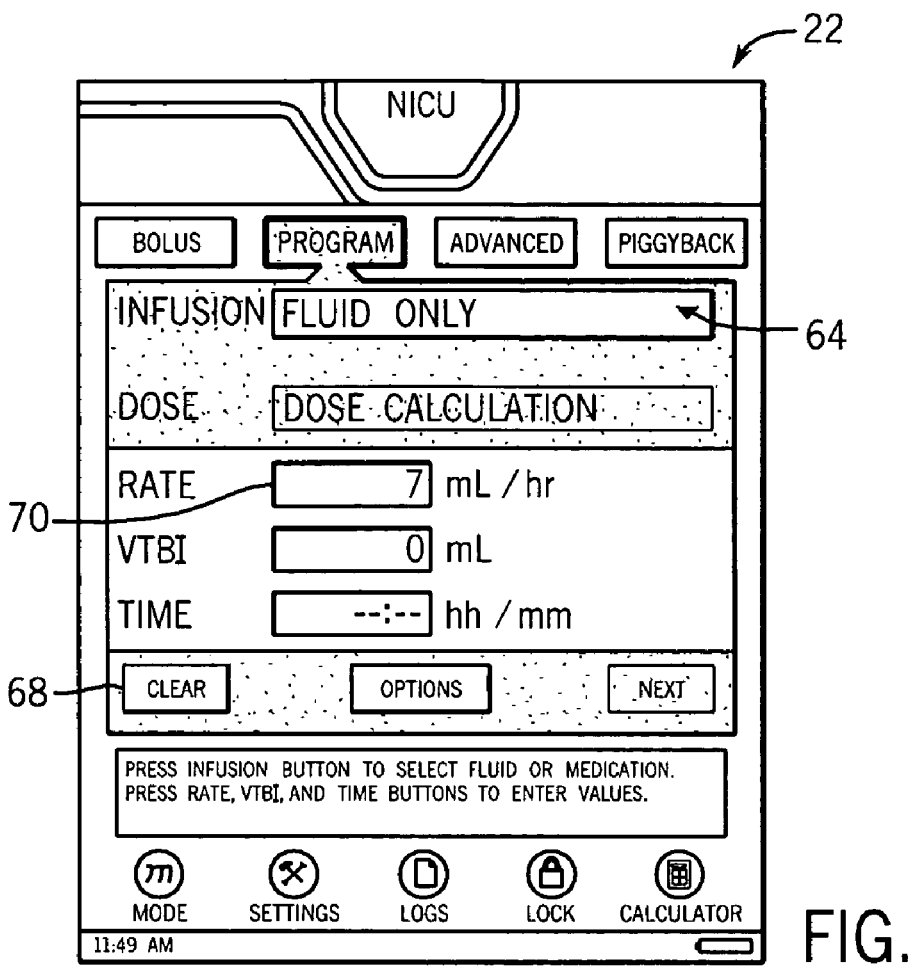

Referring to FIG. 17, suppose that the user had been entering or keying in data in a first graphical object 70 (in this case the number "7" is entered). The first graphical object 70 is represented here as a data entry field for illustrative purposes only, and could instead be any other type of graphical object. This entered data can be cleared by selecting the dual function clear/cancel button 68, which is normally displayed as a selectable clear button that provides the clear function when key-in data entry fields are accessed. Once the data is cleared, the object 70 reverts to its default or initial value or view. In the case of the rate, the initial or default value would be zero. In the case of time the default would be "--:--".

Suppose instead of clearing the entered data in the first graphical object 70 in FIG. 17, the user activates the explode button 64 to provide access to a second graphical object 72, that is, return to the drug selection screen shown in FIG. 15. The second graphical object 72 is shown here as a data entry field for illustrative purposes only, and could instead be any other type of graphical object. In the case illustrated, the second graphical object 72 overlays the first graphical object 70. Alternatively, the second graphical object 72 only partially overlays the first graphical object 70.

With reference to FIG. 15, the dual function clear/cancel button 68 is then displayed as a selectable cancel button that operates to cancel or remove the second graphical object 72 with a first activation by a user. The dual function clear/cancel button 68 is then locked out or inactivated for a given period of time after the first activation to prevent an inadvertent second activation by a user, and presents a visual indication of the inactive state of the button 68, as illustrated by stippling of the button 68 in FIG. 16. This delay prevents an inadvertent double activation of the button 68, which would result in inadvertent clearing the "7" from the data entry field 70.

With reference to FIG. 17, after the first activation by a user and once the required delay is completed, a visual indication of the clear function is made on the button 68, as shown by the lack of stippling on the button 68. As stated above, the dual function clear and cancel button 68 now operates to clear user entered content from the first graphical object 70 with a second activation by a user.

With reference to FIGS. 1 and 5F, the graphical user interface 26 provides an area sensitive scrollbar 74 on screen 22. The area sensitive scrollbar 74 provides for cycling through a list of selectable information 76 at various speeds.

Only a portion of the list of selectable information 76 is presented on screen 22, resulting in a displayed portion and a non-displayed portion. The area sensitive scrollbar 74 is positioned adjacent to the viewable or displayed portion of the list of selectable information 76. Upon activation of the area sensitive scrollbar 74 by a user, the part of the list of selectable information 76 that is the displayed portion is adjusted, i.e., the user can selectively scroll through the list 76.

The area sensitive scrollbar 74 is provided with a first weighted position 78 and a second weighted position 80. The first weighted position 78 scrolls through the list of selectable information 76 at a first given scroll rate when activated by a user. The second weighted position 80 scrolls through the list of selectable information 76 at a second given scroll rate when activated by a user, where the first and second given rates are not equal. More preferably, the second given scroll rate is greater than the first given scroll rate. The area sensitive scrollbar 74 has a center position 82 at which the scroll rate is zero.

The area sensitive scrollbar 74 also has a third weighted position 84 and a fourth weighted position 86. Like the first and second weighted positions 78 and 80, the third and fourth weighted positions 84 and 86 have unequal scroll rates. More preferably, the fourth scroll rate is greater than the third scroll rate. The third and fourth weighted positions 84 and 86 scroll through the list of selectable information in a direction opposite to the first and second weighted positions 78 and 80.

The center position 82 is located between the third and first weighted positions 84 and 78. The fourth weighted position 86 is located adjacent the third weighted position 84 and the second weighted position 80 is located adjacent the first weighted position 78. The positions 78, 80, 82, 84, and 86 are graphically presented as separate items.

Activation of the scroll element with a click and hold action by the user allows continuous scrolling in any direction. The rate and direction of scrolling varies based on the position 78, 80, 82, 84, and 86 activated by a user at any given instant during the click and hold action. Generally, the farther from the center position 82 the user clicks, the faster the rate of scrolling. The user can also quickly change the direction and rate of scrolling by selecting a different position, which makes browsing through a list extremely efficient regardless of the size of the list.

In another embodiment, activation of the scroll element with successive taps by the user at a given location on the scroll element allows continuous scrolling. The rate and direction of scrolling varies based on the position 78, 80, 82, 84, and 86 activated by a user at any given instant during the tapping action. Generally, the farther from the center position 82 the user taps, the faster the rate of scrolling. The rate of scrolling can also be responsive to the rate of tapping.

In another embodiment, activation of one of the positions 78, 80, 82, 84, and 86 with an individual tap or click action by the user can allow quick incremental jumping in predefined increments through the list of selectable information 76 to a given part of the list of selectable information 76. For example, FIG. 5F shows a portion of a list of selectable information 76 beginning with "Ceftazidime". An initial individual click action by the user to position 78 results in skipping or scrolling down X positions, where X=2 for example, through the list of selectable information 76 to "Ciporfloxacin". Likewise, an initial individual click action by the user to position 80 results in scrolling down Y positions, where Y=4 for example, through the list of selectable information 76 to "Dobutamine". Scrolling up through the list can be accomplished in a similar manner by clicking or touching positions 84 or 86. The number of positions X and Y that are jumped may be unrelated or may be related by a particular mathematical function, such as a linear equation as shown in the above example where Y=2X or an exponential equation. One skilled in the art will appreciate that X or Y can be set approximately equal to the number of selectable items concurrently displayed on the screen 22 to achieve a convenient page down or page up result.

Figure 10:
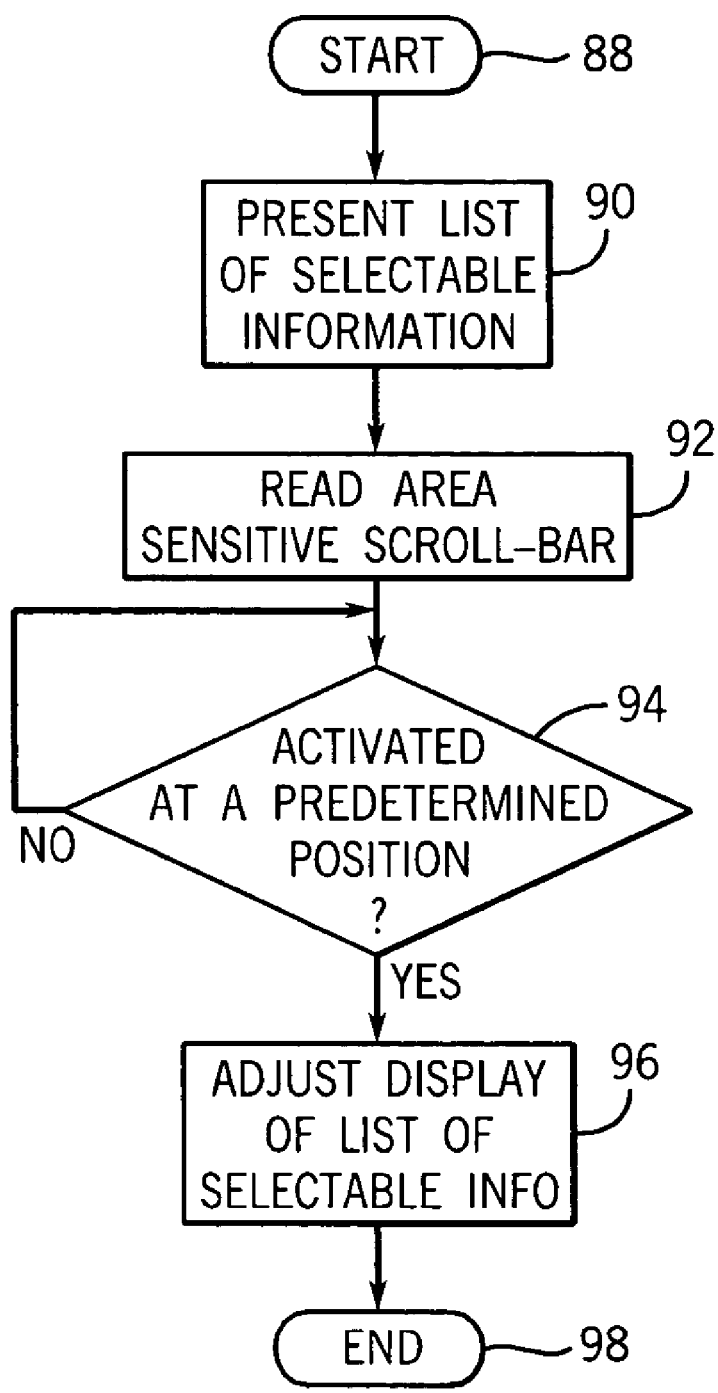
FIG. 10 is a flow chart of an area sensitive scrollbar of the medical device for cycling through lists of selectable information according to the present invention.
Figure 11:
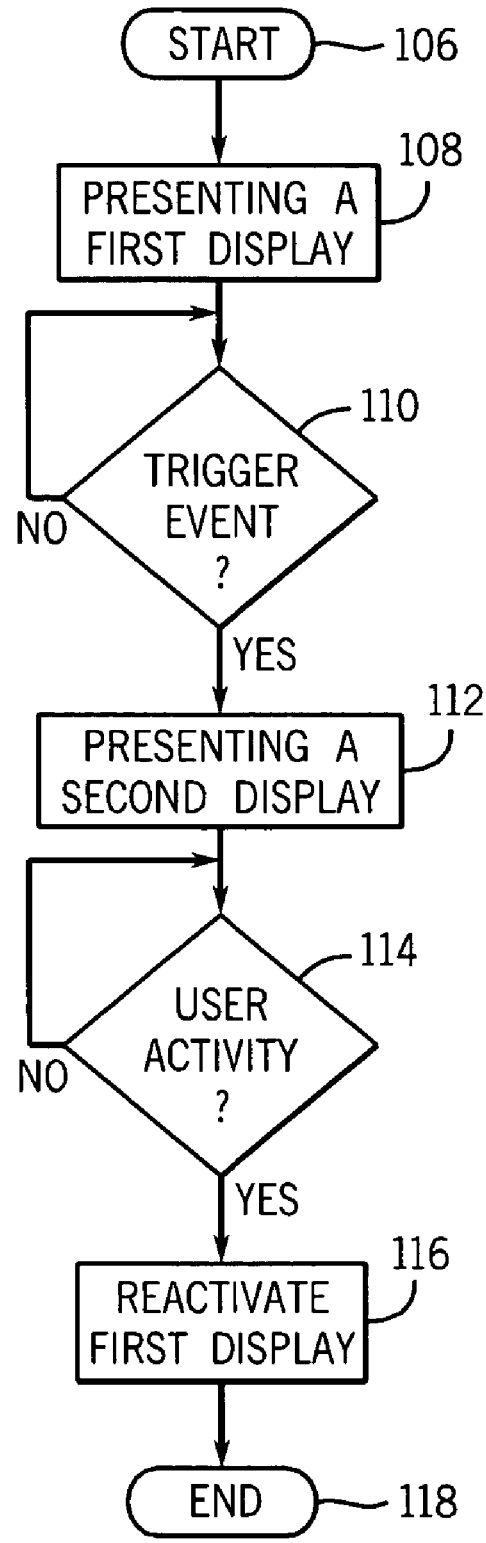
FIG. 11 is a flow chart of a screen saver mode of the medical device for adjusting screen brightness and the information presented based on feedback from an ambient light detector and on other operating conditions.

With reference to FIGS. 1, 5F and 10, the graphical user interface 26 program in the medical device 10 begins at a block 88 and proceeds to block 90 where it supplies the list of selectable information 76 and presents only a part of the list of selectable information 76 on the screen 22. Thus, the list of selectable information 76 has a displayed portion and a non-displayed portion. Once the list of selectable information 76 is presented on the screen 22, the graphical user interface 26 proceeds to block 92 where it reads the area sensitive scrollbar 74. Once the area sensitive scrollbar 74 is read, the graphical user interface 26 proceeds to decision block 94 where it determines whether the area sensitive scrollbar 74 has been activated at a predetermined position. Once the graphical user interface 26 determines the predetermined position activated, the graphical user interface 26 proceeds to block 96 where it adjusts the display of the list of selectable information at a given scroll rate or skip rate based on the predetermined position activated. The graphical user interface 26 process is then complete and ends in block 98. To stop scrolling, the user merely moves the finger or cursor away from the hot scroll area or back to the center zero position 82.

With reference to FIGS. 1, 2, 2A, 5, 5A and 11, the graphical user interface 26 provides a screen saver mode, with multiple display options, presented on screen 22 based on any number of operating conditions. The graphical user interface 26 generates a first display of given amount of operation data regarding the operation of the medical device 10 on the screen. The first display includes an operational menu, icons for user interactions with the medical device 10, and pertinent medical device 10 operating status all shown on screen 22.

The graphical user interface 26 selectively replaces the first display with a second display at a trigger event. For example, the second display can be a screen saver type display. The trigger event is based on any number of conditions or combination of conditions, including but not limited to: a manual trigger event order from the user, time elapsed from last user interaction with the medical device 10, the status of the medical device 10 (infusion stopped for instance), a count down to an infusion, and ambient light conditions at or around the medical device 10.

With reference to FIG. 1, the graphical user interface 26 monitors light levels detected by a photo sensor 100 (see FIG. 2) to adjust screen 22 brightness and as a trigger event described above. Thus, the screen 22 brightness is adjusted based on the ambient light feedback from the photo sensor 100. In the context used herein the term brightness should be understood as including but not limited to contrast, illumination output, and power consumption. In conditions where the graphical user interface 26 determines that the ambient light feedback from the photo sensor 100 is above a set threshold, the graphical user interface program 26 sends a message to the processor 18 to increase brightness on the screen 22. This ambient light feedback compensation is dynamic based on room lighting conditions. This brightness or intensity may be lower or higher depending on the trigger conditions. For example, the screen 22 becomes brighter if an alarm is sounded or if the medical device 10 detects that the user is operating the medical device 10; conversely, where the light level is low or the medical device 10 has timed out since the last user interaction, the screen 22 becomes dimmed.

With reference to FIGS. 2 and 5, the second display can include a data subset of the given amount of operation data found in the first display (FIGS. 2A and 5A). In FIGS. 2 and 5 the second display data subset is selected from a group of data that may include the channel identification, clinical care area, limit status, drug name, drug concentration, units, rate and volume (including but not limited to VTBI) of an ongoing infusion. Alternatively, the second display data subset may include dose, dosage, alarm information, current time, elapsed time in alarm status, and assigned patient identification information. In FIG. 5Y, the first display data includes the status of the medical device. As shown, the first display indicates the status of the medical device by displaying a "stopped program" message on screen 22. One skilled in the art will appreciate that similar status information can be included on the second display. In FIG. 5Y, the first display data includes a timer count down to a drug infusion including drug identification information. As shown, the medical device 10 will start infusing dobutamine at 32.6 mL/hr when the Start Program button is touched and the infusion will take 6 hours and 9 minutes.

Additionally, as shown in FIGS. 2 and 5, one or more of the corresponding values of the second display data subset are presented in a font size larger than the given size of those values in the first display shown in FIGS. 2A and 5A. Further, the brightness of the second display 104 is adjusted based on the ambient light conditions near the medical device 10, as described above with regard to FIG. 1. Additionally, the graphical user interface 26 may present the second display data subset so that it scrolls across the screen 22. Vertically elongated or "tall man" fonts can be used for letters, numbers or other information in FIGS. 2 and 5.

When the user desires to operate the medical device 10 again, any interactive activity between the user and the medical device 10 (by touching the screen 22 for example) results in removal of the second display and reinstatement of the first display with its information. A password may be required to deactivate the second display before the first display 102 is restored.

With reference to FIGS. 1, 2, 2A, 5, 5A and 11, in operation, the graphical user interface program 26 in the medical device 10 begins at a block 106 and proceeds to block 108 where it presents the first display on the screen 22. Once the first display is presented, the graphical user interface 26 proceeds to decision block 110 where it determines if a trigger event has occurred. Once the graphical user interface 26 determines that the trigger event has occurred, it proceeds to block 112 where it presents the second display on the screen 22. The graphical user interface 26 then proceeds to decision block 114 where it determines whether there has been any user activity. Once the graphical user interface 26 determines that user activity has occurred, it proceeds to block 116 where it reactivates the first display on the screen 22. The graphical user interface 26 process is then complete and ends in block 118.

Figure 12:
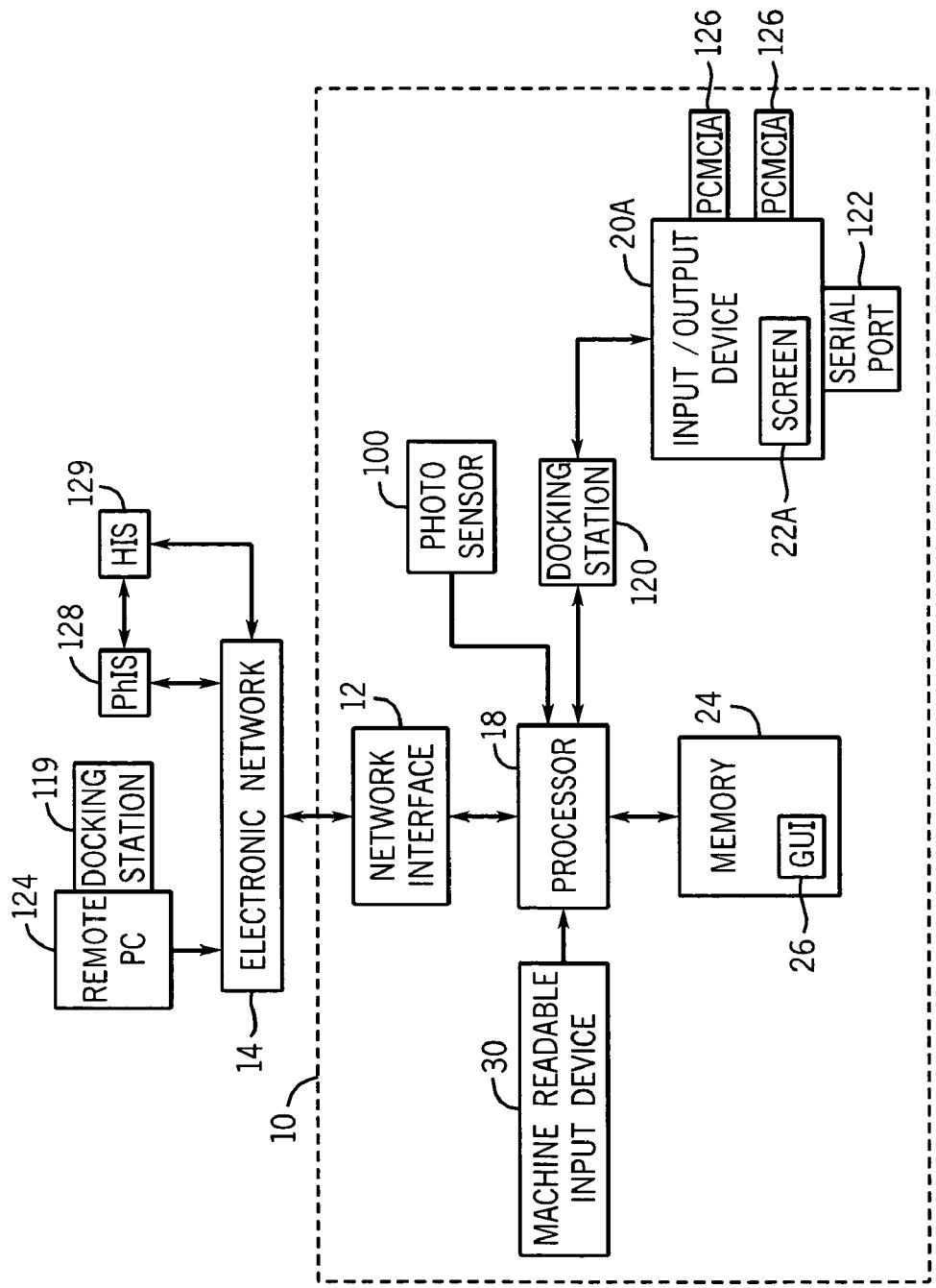
FIG. 12 is a schematic diagram of the device according to another aspect of the present invention.

With reference to FIG. 12, the screen 22 can be incorporated in a removable user interface 20A to the medical device 10. In this embodiment, the removable user interface 20 operates on a "personal data assistant" or PDA. The removable user interface 20A can be removed from the medical device 10 at any time, just as a PDA used in conjunction with a personal computer 124 may be removed from the docking station 119 at any time. This allows the clinician to set up the medical device 10 and patient information at a position remote from the medical device 10, and then activating the medical device at the bedside by placing the removable user interface 20A into a docking station 120 at the front of the medical device 10. When docked, the removable user interface 20A becomes the primary user interface for the medical device 10, displaying a screen 22A, which shows the (preprogrammed) infusion parameters. If satisfied with these, the clinician can use the screen 22A as a touch screen (in the same manner as a PDA is normally used) and hit a start button to begin the infusion. Additionally, infusion parameters can be altered by other buttons on the removable user interface 20A touch screen (buttons dedicated for titration for example). Data from the removable user interface 20A is transferred to the processor 18 that controls the medical device 10 via a serial port (or other interface including but not limited to USB or Ethernet) connection 122 of the removable user interface 20A or wirelessly. Data from the processor 18 also can be transferred to the removable user interface 20A, so that infusion history and alarm history are available to the clinician.

At the termination of infusion, the removable user interface 20A may be removed from the medical device 10 by the clinician and returned to a cradle or docking station 119 at a remote PC 124, where infusion history can be transferred to other clinical record keeping software programs and/or set up for other patients. The infusion medical device 10/removable user interface 20A combination can also act as the traditional "docking station" cradle for the removable user interface 20A, such that the removable user interface 20A can connect to any PC 124 via its serial port 122 for example. This would allow the medical device data that has been moved onto the removable user interface 20A to be downloaded to the PC 124. Further, one removable user interface 20A can be used to control multiple medical devices 10, through daisy chaining from the serial port 122.

Further, multiple PCMCIA slot 126 interfaces are added to the combined removable user interface 20A/medical device 10 assembly. The purpose of these PCMCIA slots 126 is to allow additional devices (that are compatible with the PCMCIA slots 126) to be plugged in and communicate with the removable user interface 20A and medical device 10. For example, a wireless LAN card (not shown) could occupy one of the slots 126. This allows data from the removable user interface 20A and hence the medical device 10 to be transferred to a wireless network 14 and in addition to receive data from the network 14. For example, data can be downloaded to the removable user interface 20A directly from a Pharmacy Information System 128 or Hospital Information System (HIS) 129, without passing through the medical device 10. Other devices that could fit into the PCMCIA slots 126 are compatible monitoring devices. The PCMCIA slots 126 may also accommodated or include sticks, cards or other memory or data storage devices.

Figure 13:
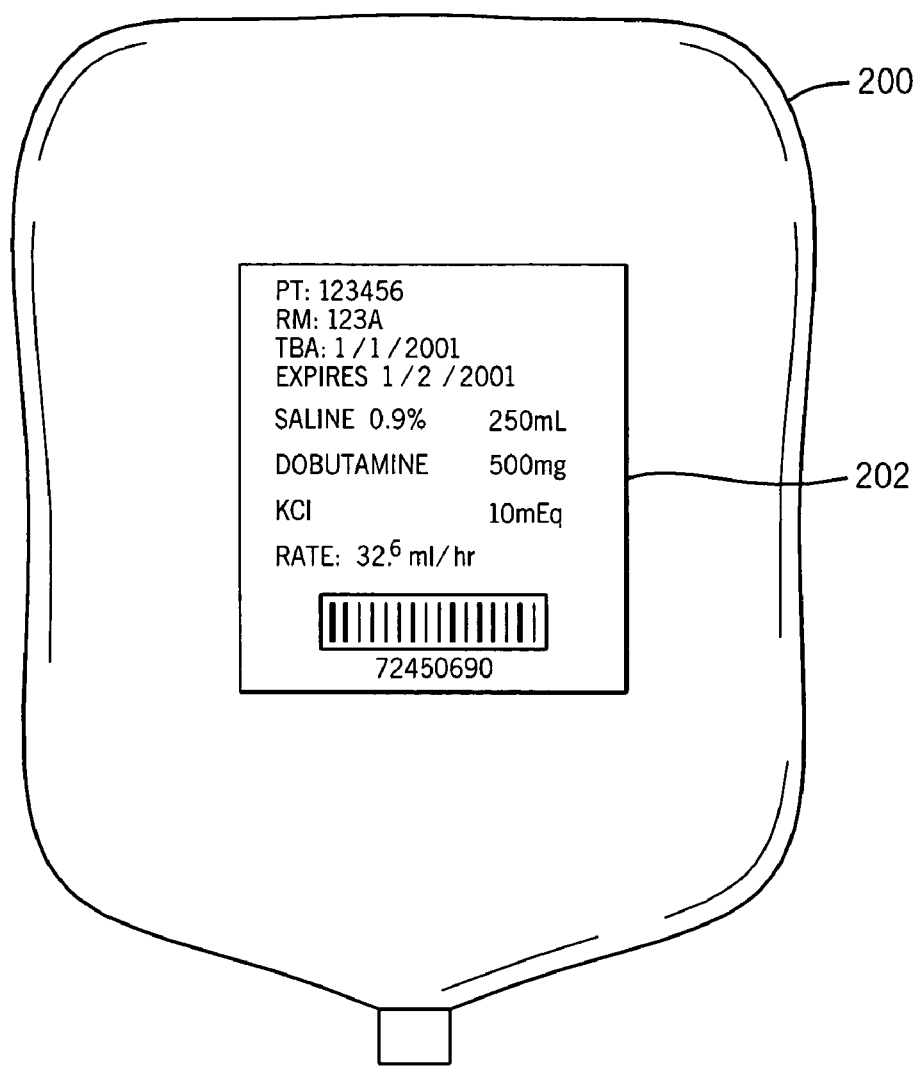
FIG. 13 is a front view of a labeled container for one or more therapeutic agents.
Figure 14:
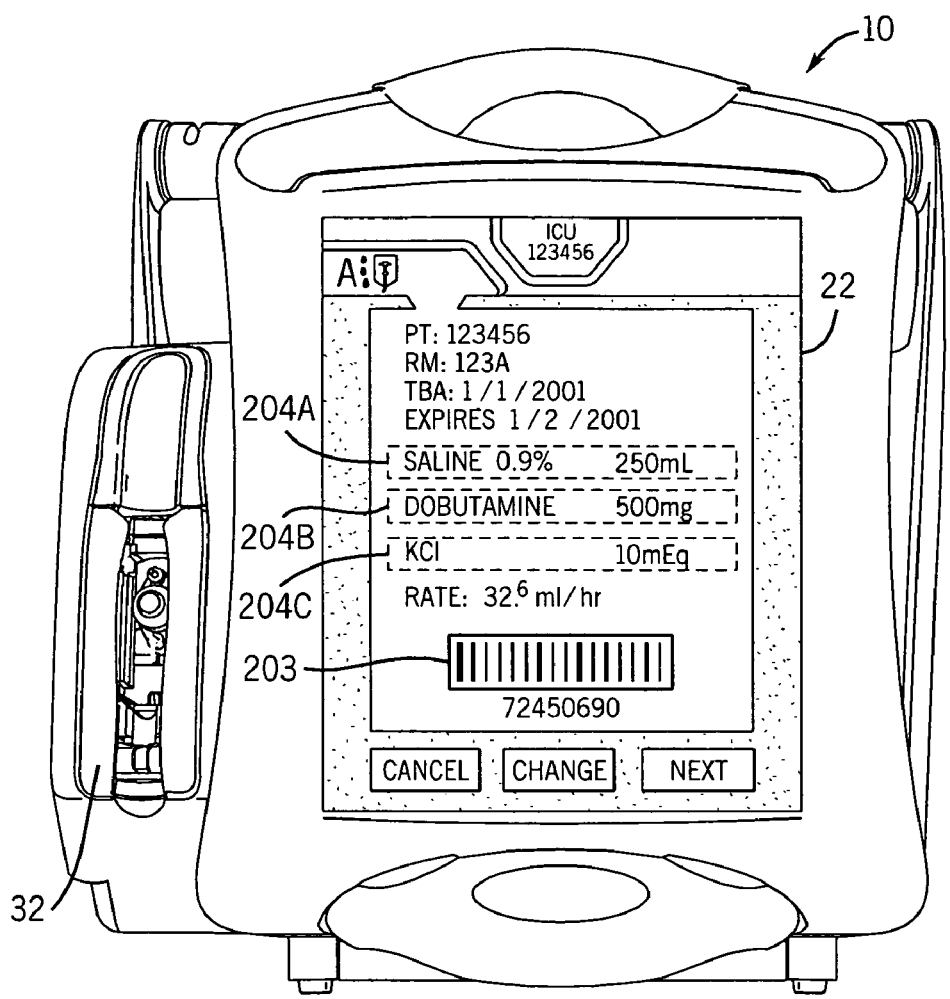
FIG. 14 is a front view of a medical device with a display screen having areas for displaying an image of the entire label or portions thereof according to the present invention.

FIGS. 13-14 illustrate that the present invention provides means and methods for displaying on a medical pump 10 a complete medication order defined by a plurality of therapeutic agents of predetermined amounts contained in a single container 200. Conventional medical pumps lack this capability.

As best seen in FIG. 13, the container 200 has a label 202, which is typically smaller than the dimensions of the screen 22. The container 200 contains at least one therapeutic agent and can, in practice with the present invention, contain a plurality of therapeutic agents. Often a drug is premixed with a diluting agent such as water or saline. A lyophilized drug can be held in a frangible barrier associated with the container and released into the container just prior to administration. Sometimes several compatible or complementary drugs are formulated or mixed together to form a "cocktail." Ideally, some portion of the label 202 indicates which therapeutic agents are in the container 200. In some cases, the drug manufacturer fills the container 200 and applies the label 202. In other cases, the caregiver or the hospital pharmacy prepares the contents of the container 200 and applies a label 202. Various information can be on the label 202, including without limitation the drug or therapeutic agent name, drug or agent concentration, amount, drug manufacturer, NDC code, date of preparation, preparing pharmacist/caregiver, prescribing physician, date prescribed, date to be administered, care facility name, patient name or ID, and expiration date. A machine-readable tag 203, including but not limited to a bar code or RFID tag, on the label 202 can contain all or any portion of this information.

As best understood in FIGS. 13 and 14, the pump 10 includes a pump channel 32 adapted to deliver one or more therapeutic agents from the single container 200 to a patient (not shown). A display screen 22 is attached to the pump channel 32. The display screen 22 has a first area 204A for displaying information regarding a first therapeutic agent contained in the container 200 and a second area 204B for concurrently displaying information regarding a second therapeutic agent contained in the container 200. Depending on the particular prescription ordered by the physician and prepared by the pharmacist or other appropriate personnel, the container 200 can contain additional therapeutic agents. Thus, the display includes a third area 204C for displaying information regarding a third therapeutic agent contained in the container 200 while the information regarding the first therapeutic agent and the second therapeutic agent is displayed concurrently in the first area 204A and second area 204B respectively. The prescribed and/or actual rate of the infusion and other information including, without limitation, patient ID, room number, date to be administered, expiration date of the administration order or the drug(s) in the container can be provided on the display screen 22.

The information regarding the therapeutic agents can include data selected from a data set including, without limitation, the name of the respective therapeutic agent and the predetermined amount of the respective therapeutic agent contained in the container 200. The name of the therapeutic agent can be its chemical formula or other identifying term. The predetermined amount of the therapeutic agent in the container 200 can be displayed or expressed in conjunction with displayed units of measure selected from a group consisting of drug units, milliliters (mL), milligrams (mg), and milliequivalents (mEq).

The screen 22 of the medical pump 10 provides a method of displaying a medication order defined by a plurality of therapeutic agents of predetermined amounts contained in a single container 200. The method includes the steps of 1) providing a display screen 22 attached to a pump channel 32, and 2) simultaneously displaying on the display screen 22 information regarding at least two of the plurality of therapeutic agents contained in the container 200. The information displayed is selected from a group that includes but is not limited to the therapeutic agent name and therapeutic agent amount. Advantageously, the information is displayed on a single common display screen 22. The information can be displayed in a variety of formats, including but not limited to giff, html, tiff, rtf, pdf and jpg.

A medication order prescribed to be delivered by a medical pump 10 from a container 200 equipped with a label 202 easily can be verified by providing a sufficiently large display screen 22 (preferably attached to a pump channel 32 of the medical pump 10), supplying an electronic image of a portion of the label to the medical pump, and displaying the electronic image on the display screen 22 of the medical pump 10. The electronic image can be generated or supplied in a variety of ways, including but not limited to, scanning and transmitting a bar code 203 from a portion of the label 202 with a bar code reader 30 (FIG. 3), and making a digital photograph of some portion or all of the container label 202. The caregiver can visually compare the displayed electronic image with the portion of the label on the container 200. Alternatively, as understood in view of FIGS. 1 and 12-14, the processor 18 of the pump 10 can compare the electronic image supplied by the image generator 30 from the container to a reputed electronic image of the container label portion supplied by a second source, including but not limited to a hospital information system (HIS) or pharmacy information system (PhIS) 128. Preferably, the reputed electronic image of the container label portion is generated earlier, such as when the physician's medication order is prepared by the pharmacist. The step of comparing the electronic image with the reputed electronic image of the label from the second source includes the steps of transmitting the reputed electronic image to the medical pump 10 and displaying both the electronic image and the reputed electronic image on the screen 22, 22A simultaneously or concurrently. Alternatively, the processor 18 and graphic user interface 26 can merely display the image and the reputed image concurrently or simultaneously on the display screen of the pump for the caregiver to compare and verify. The processor 18 of the pump 10 includes a memory containing code for populating a data input screen on the pump with information from the electronic image of the label after the comparing step is successfully completed.

Thus, it can be seen that the invention provides a system for verifying a medication order to be dispensed from a container 200 having a label 202. The verification system includes a medical pump 10 including a processor, a pump channel 32 and a display screen 22 attached to the pump channel 32 and connected to the processor 18; a label image generator 30 for transmitting an electronic image of a portion of the label to the processor 18 of the medical pump 10; and the display screen 22 is adapted to display the portion of the label at least at full size.

From the description above it should be apparent that the large color LCD-touch screen 22, 22A of the pump 10 has many advantages and allows the healthcare practitioner to verify, monitor and program fluid delivery in a variety of weight-based and surface area-based units such as micrograms/kg/hour, grams/m$^2$/hr, and other delivery specifications. The display screen 22, 22A provides visible indication of several functions including active pump operations, alarm and program status, and fluid flow parameters.

Figure 6A:
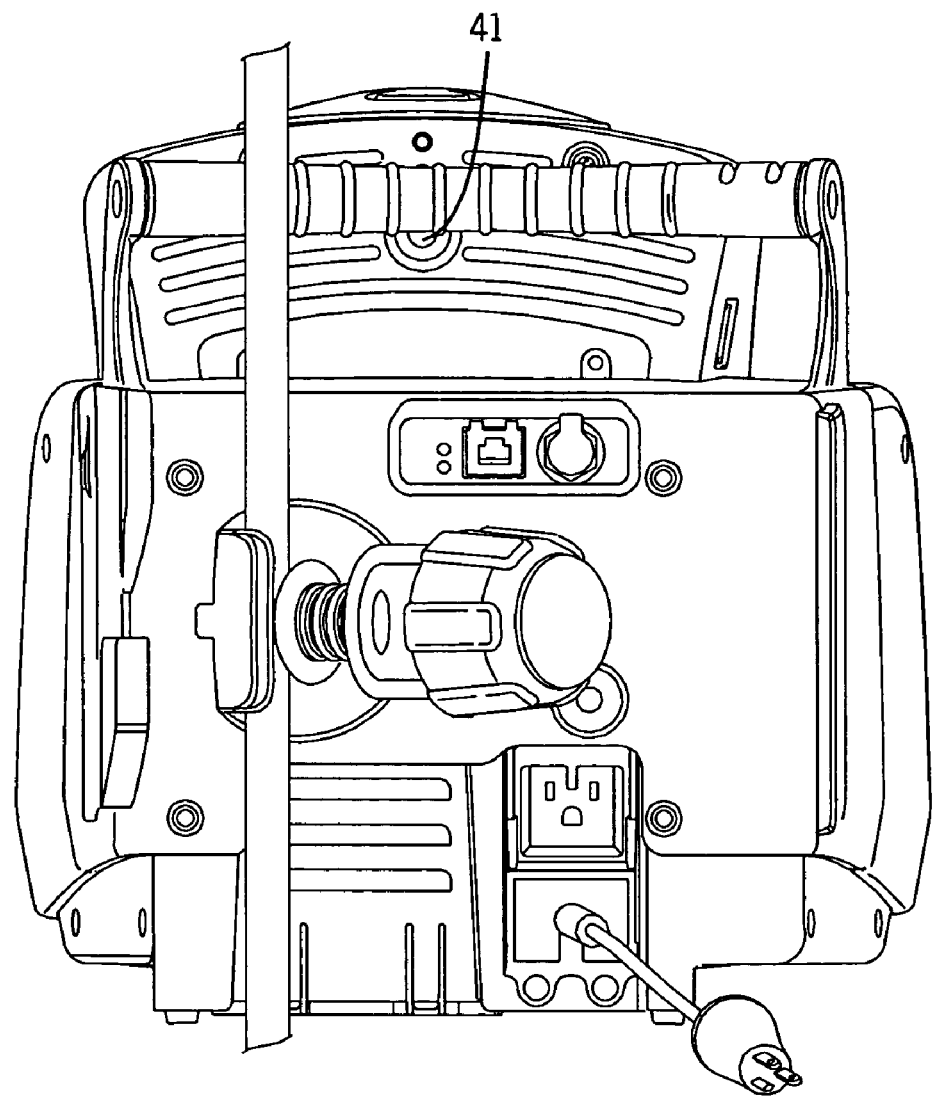
FIG. 6A is a partial rear view of one of the medical devices of FIG. 6, which illustrates the position of the display screen lockout button of the present invention.

Referring again to FIGS. 2, 4, 5, 5A-5L and 6A, the present invention provides at least two means by which the user can interface with the pump 10: dedicated or fixed tactile infuser buttons, and images of buttons on the LCD-touch screen 22. The fixed tactile buttons 33, 35, 37, and 39 provide the following functions: LOAD/EJECT button 33—opens and closes the cassette carriage; ON/OFF button 35—turns power on and off; ALARM SILENCE button 37—silences a silenceable alarm for a specified period of time, for example two minutes; and EMERGENCY STOP button 39—stops all channels. As seen in FIG. 6A, another tactile button, the Cleaning Lock Button 41 located on the rear of the pump, activates and deactivates the touch screen 22. When the touch screen 22 is deactivated, a user can touch the screen for cleaning, handling, or other purposes, even while the pump power is on, without having any impact on the processor 18 or the operation of the pump.

The LCD color touch screen 22 allows the user to access and use on-screen button images and data entry fields. The touch screen 22 uses a membrane over the LCD display so a single keypress does not cause significant infusion pole movement nor is it mistaken for a double keypress. The touch screen also accommodates a keypress whether the user is wearing wet gloves, dry gloves, or no gloves.

LCD touch screen buttons images 43, 45, 47 and 49A-49E are located as shown in FIG. 2, 2B, 5 or 5B and perform the following functions: Patient Information Tab 43—displays the clinical care area, preselected patient information (including without limitation name, ID number, etc.), and provides access to a more detailed patient information screen (FIG. 5B); Channel Level Therapy Buttons 45—accessed by button images on the infuser touch screen, are used to select an infusion therapy; Program Level Buttons 47—accessed by pressing areas, drop-down list triangles, boxes or text boxes on the programming screen, are used to select dose parameters of an infusion; and Device Level Buttons 49A-49E at the bottom of the touch screen are used to display and control device level features, including without limitation Mode 49A (for example, Operational or Biomed), Logs 49B, Locks 49C, Settings 49D, and Calculator display 49E. A wireless indicator image 102 displayed at the bottom of the screen 22 indicates that the device 10 is connected and ready for communication.

By using the Channel Level Therapy Buttons 45 and the Program Level Buttons 47, the healthcare practitioner can program each individual channel of the pump with specific fluid therapies in a variety of weight- and body surface area-based units such as micrograms/kg/hour, grams/m$^2$/hr, and other delivery specifications for the following modes: (Program 45B) Basic Therapy—includes dose calculation, which allows dose rate programming based on volume to be infused (VTBI), drug amount, infusion time and drug concentration and simple rate programming that allows programming of volumetric rate (mL/hr) based upon VTBI and time; Bolus delivery 45A—allows user to program a single uninterrupted discrete delivery based on dose amount and time (the bolus can be delivered from the primary or a secondary container); Piggyback delivery 45D—allows user to program the delivery of a secondary infusion, to be delivered through the same cassette as the primary infusion (the primary infusion is paused until the piggyback VTBI completes); and Advanced Programming 45C. Advanced Programming mode 45C provides various types of programs including: Multistep—which allows a sequential delivery of fluid in up to 10 steps, with fluid volumes and delivery rates programmable for each step based on Rate and Volume or Volume and Time; Variable Time—which allows up to 24 dose calculation steps at specified clock times; Intermittent—a calculated dose or step to be delivered at regular intervals; and Taper—a delivery that ramps up and/or ramps down to a plateau rate.

The pump user interface or display screen 22 has a positional relationship between the pump delivery channel(s) 32, 36 and the infusion container. On a two-channel pump 10B (FIG. 2) the Channels are labeled A and B with the left side of the display screen 22 dedicated to Channel A, which is on the left side of the pump and the right side of the screen dedicated to Channel B, which is on the right side of the pump. Extensive human factors research resulted in an intuitive relationship between programming screens and their corresponding pump channels. A channel tab structure or image 58 is used to designate each channel. The tabs 58 have a three-dimensional raised look in keeping with a design theme wherein three-dimensional raised objects on the screen are selectable by touch and will link to screens containing additional detail about the pumps delivery status and state of programming.

During an infusion, the medical device or infuser 10 is in delivery mode. The delivery mode screens contain information about the progress of the infusion. There are two types of screen displays during the delivery mode: a far view and a near view. The far view delivery screen is shown in FIG. 5 for a single channel pump. The far view screen displays drug name, concentration, dose rate (if applicable) or rate, VTBI, and, if in an alarm state, the alarm name for the highest priority alarm. The far view delivery screen is shown in FIG. 2 for a multiple or dual-channel pump and is readable from a distance of about 15 feet (4.6 m). An animated drip icon 60 displayed on the tab of the active channel's delivery screen indicates an infusion is in progress. The animated drip icon 60 is displayed on every screen during an infusion.

A near view delivery screen is shown in FIG. 5A. The near view delivery screen displays drug name, concentration, dose rate, time remaining, VTBI, volume remaining, and alarm name for the highest priority alarm if in an alarm state. The near view delivery screen will switch to the far view delivery screen after a defined period of time that is configurable by the facility, for example after 20 seconds.

FIG. 5P shows a completed infusion program screen just prior to the user touching the "Next" button 104. Prior to starting any infusion, the user is required to confirm the programmed infusion by means of the confirmation screen shown in FIG. 5Q. The confirmation screen allows the user to confirm that the programmed values were correctly entered. The clinician confirms and validates the programmed values prior to pressing the start button to begin the infusion program. Generally confirmation and validation is accomplished by the caregiver visually reviewing the displayed program values for accuracy and then pressing the "Start" button 130; however, other means of confirmation and validation may include but are not limited to audible feedback or warnings generated by the pump.

The facility can establish dosing range and limits for each drug in a library of drugs utilized by the facility. As best understood in view of FIG. 1, the facility can download all or any portion of the drug library information to the memory 24 associated with the pump processor 18. Thus, the clinician will receive an alert if a programmed entry violates facility defined dosing range and/or limits. Any combination may be defined. Each drug can be associated with two types of alert levels, a "soft" limit alert or a "hard" limit alert. If the programmed dose is outside a soft or hard limit, an alert (visual and audible) will result. A software feature allows the pharmacy or authorized individual to customize the hospital drug library based on hospital Clinical Care Areas (CCAs) to meet the need of the selected hospital area/unit. For example, the programming parameters for a pediatric defined area are expected to be much different than one for an adult intensive care unit. To be able to start the infusion, the dose value entered must be within the acceptable range set by the facility or confirmed by the clinician or supervisor that the dose outside the range is in fact required for the specific patient. The clinician or user can override soft limits, whereas a hard limit requires a pass-code for an override. The pass-code is to have restricted distribution.

Figure 9A:
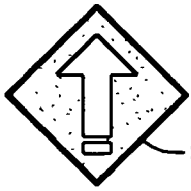
FIG. 9A is similar to FIG. 9 but illustrates infusion status icons that convey information regarding violations of soft or hard limits or the absence of such limits according to the present invention.
Figure 9A:
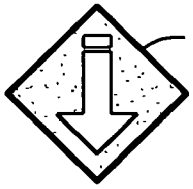
Figure 9A:
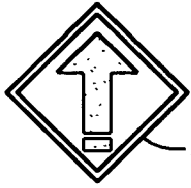
Figure 9A:
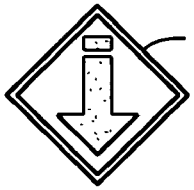
Figure 9A:

As best seen in FIG. 9A, displays or icons will appear during delivery screens to remind the clinician that the programmed therapy is outside the hospital's best practices or has no rule set applied. If the pump is delivering in the range outside a soft limit but within the hard limits, either an above the soft limit icon 57A or below the soft limit icon 57B will appear on the appropriate channel indicator tab 58 of the pump screen during delivery. Although other designs and color schemes are possible, the icons have a black arrow on a yellow rhombus-like or diamond shaped background. This shape and color combination almost universally suggests caution. The arrow points up when an upper limit is exceeded and down when a lower limit is violated.

Figure 5R:
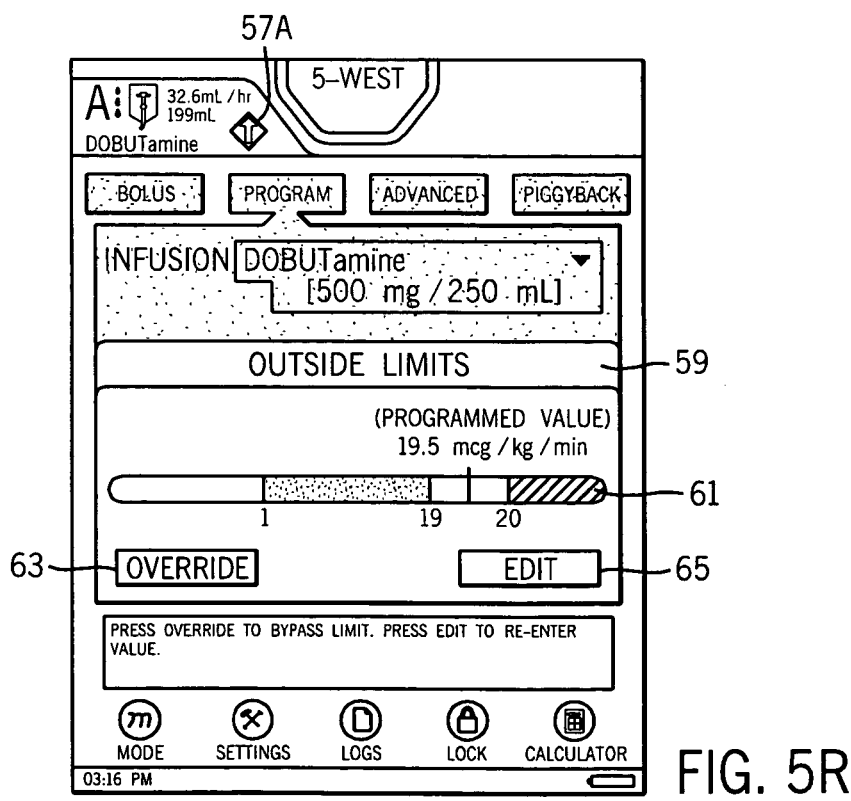

As best understood in view of FIG. 5R, an "Outside Limits" display 59 pops up in the program area of the touch screen. A numbered continuum line or bar 61 depicts the programmed value (and units) relative to the limits. Although histograms, bell curves, or other designs are possible to provide additional frequency information and different colors may be used, preferably the bar 61 is a simple multi-colored bar extending horizontally across the display 59. The continuum bar 61 is red (as illustrated by cross hatching in FIG. 5R) outside any hard limits present, yellow (shown in FIG. 5R as white) outside the soft limits when they are present, and green (shown as stippled in FIG. 5R) within the acceptable range. Thus, when the programmed value is displayed and indicated on the bar 61, the display 59 provides the user a quick, easy to understand visual diagrammatic indication of how the programmed value compares to the applicable limits and which direction it needs to be shifted to be more acceptable. "Override" and "Edit" button images 63, 65 are provided on the display 59 to override the exceeded limit or edit the programmed value respectively. Pressing the Override button 63 or the Edit button 65 removes the Outside Limits display 59 and returns the user to the Program screen.

Figure 5S:
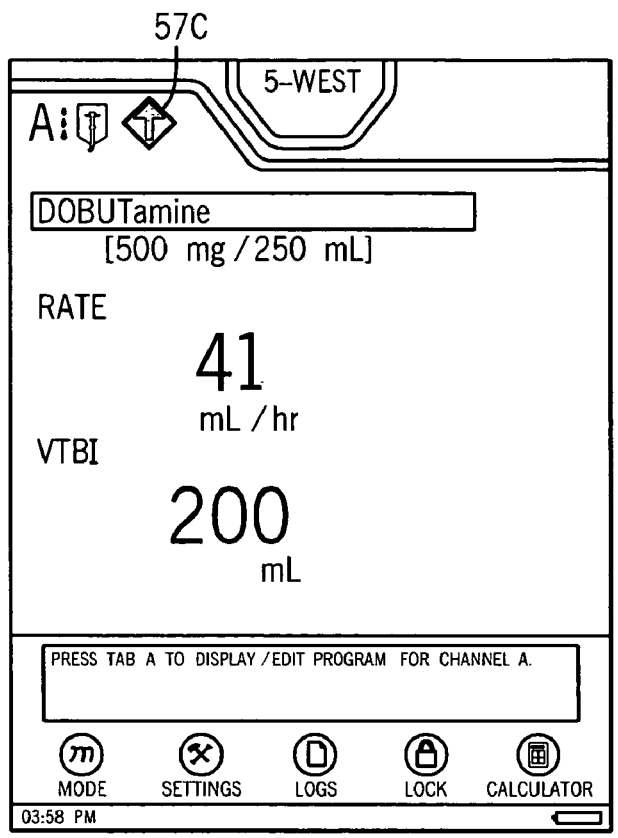

FIG. 5S shows the hard limit outside of limits message or alert being shown on a far view screen. If the pump is delivering in the range outside the hard limit, either an above the hard limit icon 57C or a below the hard limit icon 57D (see FIG. 9A) will appear on the appropriate channel indicator tab 58 of the pump screen during delivery. Although other designs are possible, the icons have a white arrow on a red rhombus-like or diamond shaped background. The arrow points up when an upper limit is exceeded and down when a lower limit is violated. The color red suggests that the user monitor the patient closely. As described above, an "Outside Limits" display 59 pops up in the program area of the touch screen and a numbered continuum line or bar 61 depicts the programmed value (and units) relative to the limits. All soft and hard limit violations are recorded in an event log and overrides are logged in a rule set override log as pump history in the memory 24.

In an emergency, the user may program the pump without drug rule sets by selecting the simple delivery mode "Fluid Only" or "Other Drug". If this is done, the event is logged in the pump's history. When a "Fluid Only" or "Other Drug" option is chosen or the drug in the drug library has no associated rule set, the "Outside Rule Set" icon 57E (FIG. 9A) appears on the appropriate channel indicator tab 58 of the pump to remind the clinician that the pump has been programmed with no limits and to review the package insert for the fluids/drugs being administered. The "Outside Rule Set" icon 57E has a white exclamation mark on a red triangle shaped background.

The present invention provides unique means and methods for programming the infusion pump 10, as best understood in view of FIGS. 5B-5Z and described below. After identifying whether the pump is being assigned to a new patient, the user can input patient data that appears on the Patient Information Tab 43. At a minimum the user must select the CCA as depicted in FIGS. 5B-5D. As indicated by FIG. 5D, the user can also input information about the patient, including but not limited to patient name, other patient ID, height, and weight. For example, touching the Patient Name area 170 or the down arrow 172, provides the data entry screen 174 shown in FIG. 5Z. This data entry screen has images of keys for entering alphabetical information, punctuation, commonly used symbols (including but not limited to +, −, &, *, %, !, [, ], ", ', >, <, and #), as well as cancel, clear and enter functions. The button labeled "123" pops up a numeric keypad 47 similar to that shown in FIG. 5L.

The user begins programming an infusion by touching the Program area 45B on display screen 22. This causes the Infusion screen 132 to appear as shown in FIG. 5E. The user then touches the Select Infusion area 134 to make a selectable drug list 76 or portions thereof stored in the memory 24 of the pump 10 appear in a scrollable drug list screen 136 as shown in FIG. 5F. The hospital or care facility can program the pump 10 so as to designate certain drugs in the drug list or library as "critical drugs" requiring a greater measure of caution in programming and administration. These critical drugs have icons on the screen 22 that are peripherally trimmed in a cautionary color, such as yellow for example, whereas less critical drugs have icons that are not so trimmed. The user then scrolls through the drug list using the hot scroll bar 74 as described above and selects the prescribed drug by touching the appropriate drug name icon 138, for example dobutamine. As illustrated in FIG. 5, the drug name and/or concentration for critical drugs can also be displayed on a yellow or other specially colored background 166. The same concept can be applied to other screens such as FIGS. 2, 2A, 2B, 5A, etc.

One unique feature of the user interface is that if the drug is available in multiple concentrations, a Select Concentration screen 140 will appear as shown in FIG. 5G when the user selects the drug. The user is then prompted to specifically verify and select the concentration that matches the prescription and the drug container. Thus, the drug and concentration are selected or programmed in two separate and distinct steps, which adds a measure of redundancy and safety to prevent medication errors. In conventional devices and methods, the drug and its concentration are listed in a single row or column in the drug library or list, displayed on the screen alone or together with adjacent portions of the list, and selected in a single step. Since the drugs are listed alphabetically and multiple concentrations of the same drug appear adjacent to each other, concentration selection errors may result.

In this example, the user has selected the concentration of 500 mg/250 mL. Once the drug and concentration are selected, the Dose Calculation area 63 becomes active as shown in FIG. 5H. The user is provided with the opportunity to have the user interface calculate a dose by touching the Dose Calculation area 63. The user interface responds by providing a Dose Calculation Screen 66 as shown in FIG. 5I. If the hospital has not pre-established the units for dosing the particular drug, the user is prompted to select the dosing units by touching the Select Units area or button 142. A pop-up Select Units screen 144 appears as shown in FIG. 5J, which allows the user to scroll through the list and select the units by touching the area corresponding to the desired units. The user interface responds by returning to the Dose Calculation screen shown in FIG. 5K and displaying the selected units. In this example mcg/kg/hr was selected as the units. If the hospital pre-established the units for the drug, the user would skip the Unit Selection step and proceed directly from FIG. 5H to FIG. 5K. In that case, the Select Units area 142 in FIG. 5K would be prefilled, inactivated, unavailable or grayed to indicate that selection was not allowed by the user. The user interface automatically grays or inactivates certain data entry areas in FIG. 5K depending on the units selected. FIG. 5K shows that the patient's weight has been previously input as 70 kg. If the patient's weight has not previously been entered the Weight area 146 or field is blank, it can be selected for data entry in the same manner as the Dose area field described below. A previously entered weight value can also be edited by touching the Weight area 146. The pump processor 18 can be programmed to automatically incorporate this change in weight into the patient information screen 148 accessed by the Patient Information Tab 43 (FIG. 5B). Alternatively, the processor can be programmed to ask the user if the change in weight should be made temporary or incorporated into the patient information screen 148. Alternatively, the pump may assume the weight change to be temporary unless the user returns to the patient information screen 148 and inputs it there. Height and BSA also can be edited in the same manner as Weight.

Alternatively as can be understood in view of FIG. 5N, if the drug is commonly prescribed and identified in the drug library as administered in mL/hr, the Dose Calculation is greatly simplified because the dose and the rate are one in the same. Thus, the Dose Calculation area becomes inactive, made unavailable, or gray and the Rate program area becomes active for data input immediately.

However, normally when the user touches the Dose area 63 in FIG. 5K, the Numerical Data Entry (keypad) area or screen 47 shown in FIG. 5L appears. The user touches number and decimal icons to key in the desired dose value 62, which is displayed as keyed by the user in the Dose area 63. The user then touches the "Enter" area 152. The user interface responds by sending the user to the screen shown in FIG. 5M. The Enter area 152 is still activated (i.e., not grayed or unavailable). The user can then touch the Enter icon, which causes the user interface to calculate the Rate. Note that all calculated values are clearly identified and designated as [Calculated] on the display screen 22. Next the user touches the VTBI area and repeats the data entry process to input the volume to be infused (VTBI). The user interface then calculates the Time. See FIG. 5P. Alternatively, the user could input the Time and the VTBI will be calculated. If the user is satisfied with all of the entered values, they can touch the "Next" area or button 104, which has now become active in FIG. 5P, or they can touch any of the active areas to revise the data entries and the values will be recalculated accordingly. When the user is satisfied, the user touches the Next area 104 and a Confirmation screen 154 appears as shown in FIG. 5Q. The Confirmation Screen 154 allows the user to verify that all entries have been made correctly and as intended.

The infusion starts after the user visually verifies or confirms the programmed values and touches the Start Program area or button 130, which clearly identifies the channel by inclusion of the appropriate channel indicator thereon. If the user is dissatisfied with the programmed values, the user can touch the Program area 45B to return to the Infusion screen 132 (FIG. 5E) where any of the values can be edited. Once the Start Program area 130 is touched, the user interface displays the near view delivery screen as shown in FIG. 5A and the drip indicator 60 starts its animation. In the absence of any user input for a predetermined elapsed time, the user interface automatically switches to the far view delivery screen as shown in FIG. 5.

Figure 5T:
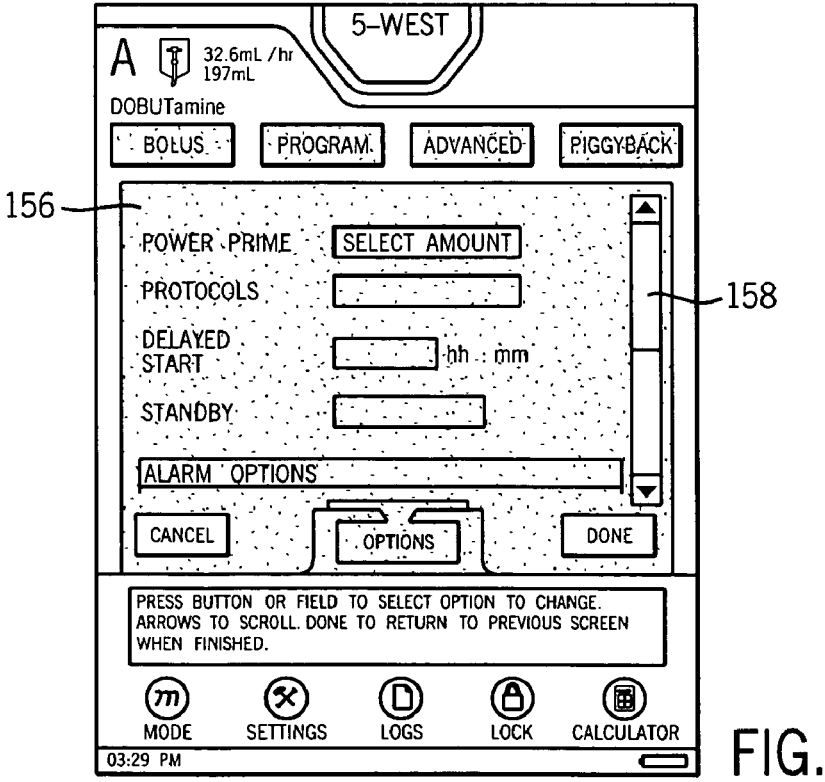
Figure 5U:
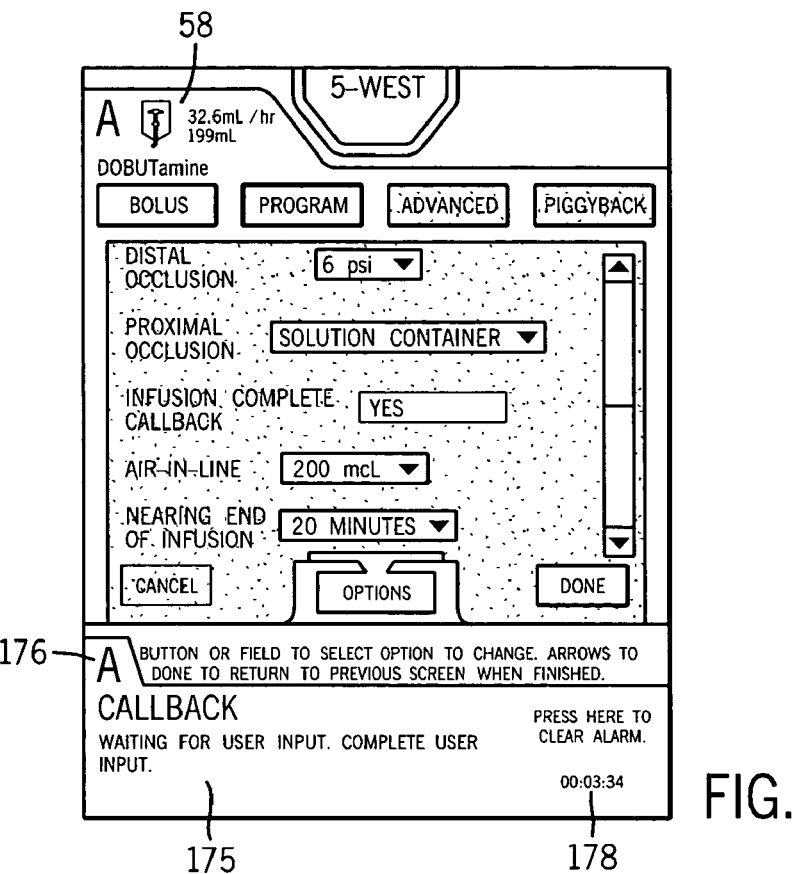

Another advantageous aspect of the invention the ability to concurrently display on the screen 22 an alarm option screen 156 for multiple, more preferably, three or more customizable alarms as shown in FIGS. 5T and 5U. A scroll bar 158 allows the user to scroll from the top of the list of alarm options shown in FIG. 5T to the bottom of the list as shown in FIG. 5U. Note that in FIG. 5U a number of the alarm options have been set but the user interface has displayed a callback alarm because it did not receive further user input within the predetermined allotted time. The alarm portion 175 of the screen includes a channel tab 176 to assist the user in determining which channel the alarm is associated with. The GUI program 26 can cause the alarm portion 175 of the screen and the associated channel tab 58 to present in the same given colors and remain continuously lit or flash intermittently depending on the urgency of the highest priority alarm. For example, in the case of the callback alarm, tab 58 and alarm portion 175 may flash yellow. Furthermore, a time display 178 is included on the alarm portion of the screen. Although other time displays are useful and possible, the time displayed in the example shown is the time elapsed since the alarm started. This feature lets the user know how long the alarming status has been present.

The large size of the screen 22 permits detailed multiple line instructions to be displayed for the benefit of the user. As many as three or more lines, plus user response buttons can be provided concurrently on the screen 22. The instructions can be related to general instructions, general alarms, a specific channel of the device, the specific drug being infused, the specific type of infusion being administered (FIG. 5V shows a bolus setup, for example), or can be helpful non-drug specific clinical advisories or instructions (FIG. 5X) are displayable.

Figure 5V:
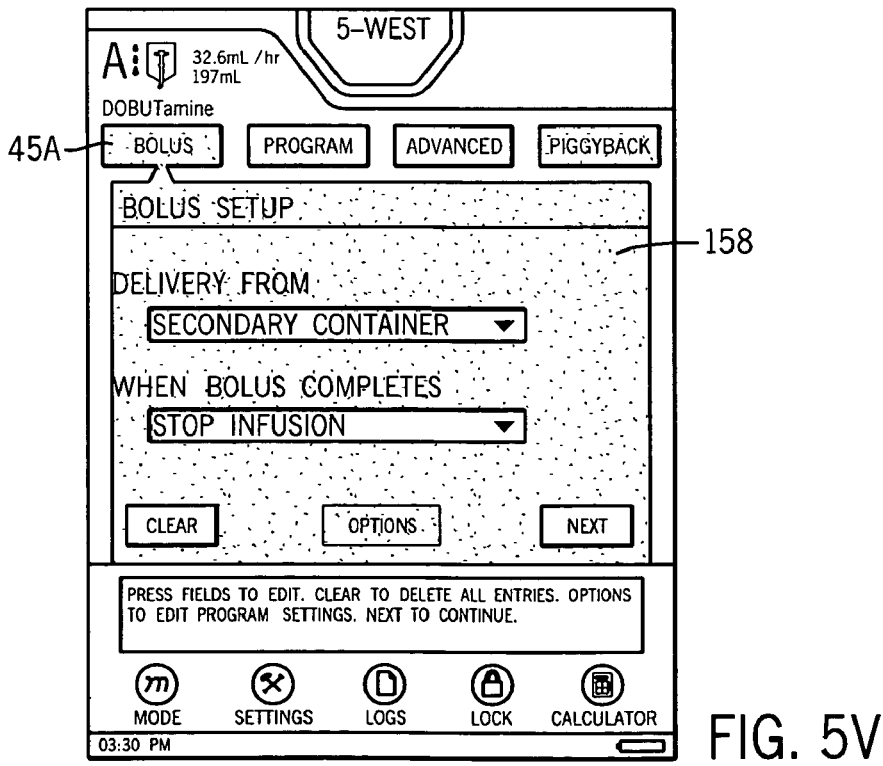

FIG. 5V shows a bolus setup screen 158. The user can program the device 10 to stop the infusion by selecting "stop infusion" as shown. Alternatively, the user can select to begin a primary, advanced or piggyback infusion upon completion of the bolus infusion, with or without a selectable time delay.

Figure 5W:
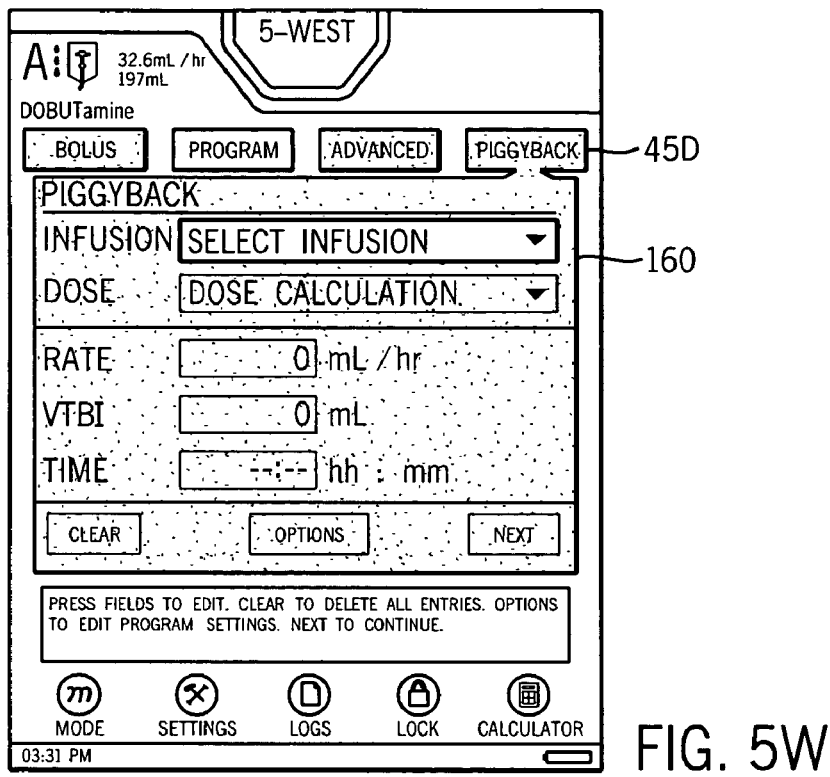
Figure 5X:
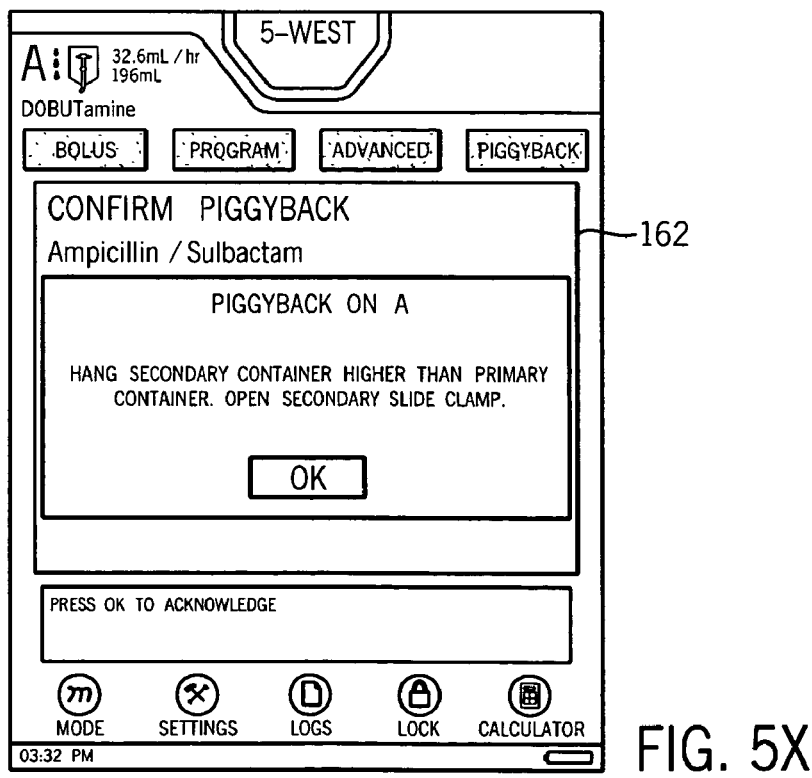
Figure 5Y:
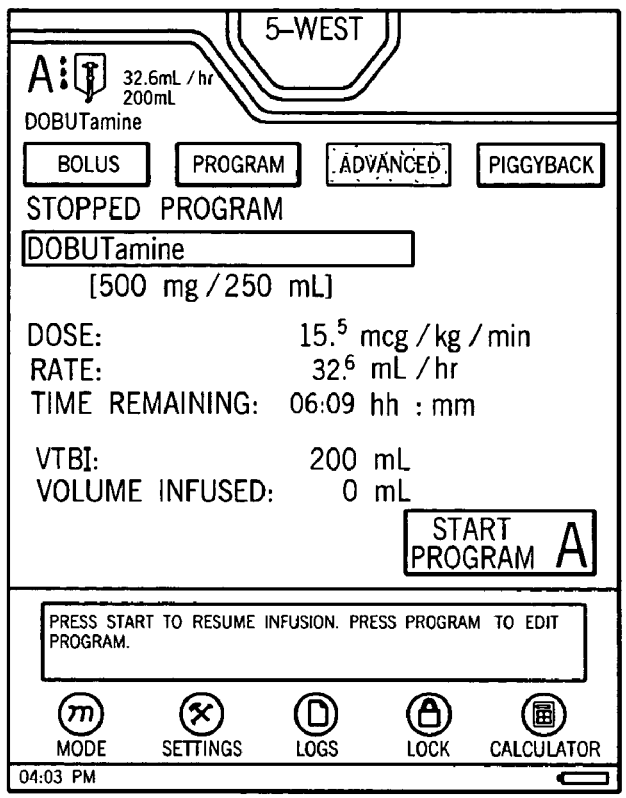
Figure 5Z:
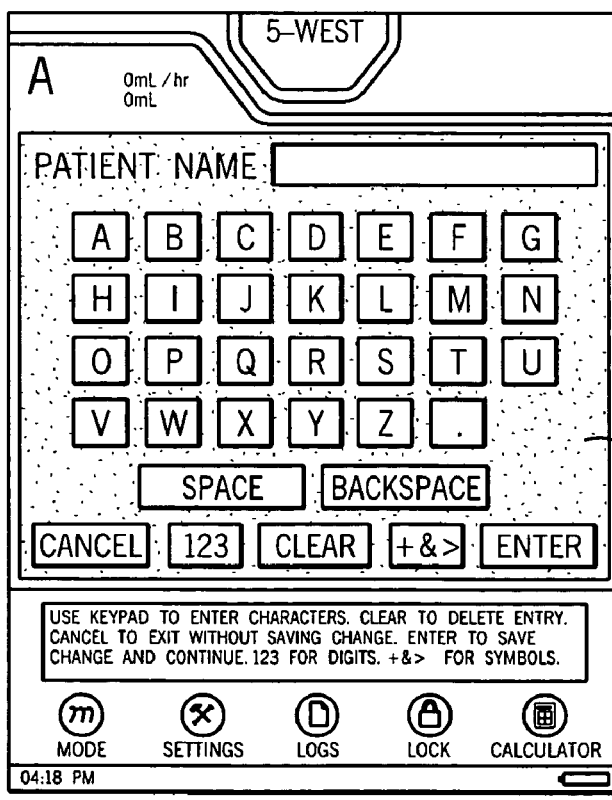

FIGS. 5W and 5X show that piggyback infusions are programmable in substantially the same manner as primary infusions. Selection of the "Piggyback" button 45D displays a piggyback infusion screen 160 that looks substantially the same as the primary infusion screen 132. After the programming is completed in the manner described above, a piggyback confirmation screen 162 is presented. The user is given drug specific information, such as the drug to be piggybacked, but is also given concurrently on the same screen the non-drug specific reminder to hang the secondary container higher than the primary container. The display also reminds the user that the piggyback is to be connected to the A channel. The user must take the appropriate actions and press the OK button 164 to acknowledge. Once the piggyback infusion is confirmed and started, the drug name and other details of the piggyback infusion will replace the details of the primary infusion on the tab 58, i.e., Ampicillin/Sulbactam, rate, VTBI, will replace DOBUTamine, 32.6 mL/hr and 196 mL.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. A medical pump, comprising:
  a display screen;
  a processing unit in electronic communication with the screen; and
  a memory coupled to the processing unit, wherein the memory contains programming code executed by the processing unit for:
  presenting a first display comprising a pump channel selection/indicator tab, pump therapy selection buttons associated with the pump channel selection/indicator tab, and a plurality of data entry fields for permitting a user to input and view pump programming data that is used by the processing unit to define a given amount of operation data regarding the operation of the medical pump on the screen; and
  selectively switching between the first display and a second display on the screen at a trigger event, wherein the second display lacks the pump therapy selection buttons but includes the pump channel selection/indicator tab and, in a font size larger than a given font size originally used to input the pump programming data, a partial data subset of the given amount of operation data.

2. The medical pump of claim 1 further comprising a photo sensor for monitoring ambient light conditions at the medical pump to trigger the event to switch between the first display and the second display such that when the monitored ambient light is less than a threshold level the first display is replaced with the second display.

3. The medical pump of claim 1 wherein the display screen is a touch screen on which the first display and the second display alternatively are presented, and wherein the touch screen is responsive to a touch on the second display to switch to the first display.

4. The medical pump of claim 3 wherein the touch screen is responsive to a touch on the pump channel selection/indicator tab on the second display to switch to the first display.

5. A method of operating a medical pump having a display screen, comprising the steps of:
  presenting a first display comprising a pump channel selection/indicator tab, pump therapy selection buttons associated with the pump channel selection/indicator tab, and a plurality of data entry fields for permitting a user to input and view pump programming data that is used by the processing unit to define a given amount of operation data regarding the operation of the medical pump on the screen; and
  inputting pump programming data into at least one of the data entry fields;
  displaying the inputted pump programming data on the first display in a given first font size;
  selectively switching between the first display and a second display on the screen at a trigger event, wherein the second display lacks the pump therapy selection buttons but includes the pump channel selection/indicator tab and, in a second font size larger than the given first font size, a partial data subset of the given amount of operation data.

6. The method of claim 5, wherein the trigger event is based on time elapsed from last user interaction with the medical pump and the step of selectively switching between the first display and the second display is done automatically without user interaction.

7. The method of claim 5, further comprising the step of monitoring ambient light conditions at the medical pump with a photo sensor and wherein the trigger event is based on ambient light conditions at the medical pump and a threshold-based feedback signal generated by the photo sensor.

8. The method of claim 7, wherein the brightness of the screen is adjusted based on the ambient light conditions at the medical pump and the threshold-based feedback signal generated by the photo sensor.

9. The method of claim 5, further comprising providing the medical pump as an infusion pump and wherein the second display partial data subset includes information selected from a group consisting of: rate, dose, dosage, volume remaining to be infused, drug identification information, status of the medical pump, current time, assigned patient identification information, a timer count down to a drug infusion, alarm information, elapsed time in alarm status, channel identification, clinical care area, limit status, and units.

10. The method of claim 5, further comprising the step of providing the display screen as a touch screen for input and output and further comprising the step of providing a touch screen keypad display on the first display, the touch screen keypad display being selected from a group consisting of an alphabetic keypad and a numeric keypad.

11. The method of claim 5, further comprising providing a visual indication of alarm status and elapsed time in alarm status on one of the first and second displays.

12. The method of claim 5, further comprising providing a patient identifying image selected from a group consisting of a photograph and a barcode on one of the first and second displays to verify that correct medical pump/patient association.

13. The method of claim 5, further comprising highlighting in a visible manner drug names designated as critical by medical personnel on one of the first and second displays.

14. A method of operating a medical pump having a display screen, comprising the steps of:
  supplying a list of selectable information;
  displaying only a part of the list of selectable information on the screen, the list of selectable information having a displayed portion and a non-displayed portion;
  providing a scroll element adjacent to a viewable portion of the screen, the scroll element being adapted to change the part of the list of selectable information that is the displayed portion by selectively scrolling through the list of selectable information at a variable scrolling rate depending upon a particular position on the scroll element that is activated by a user;
  providing on the scroll element a first weighted position and a second weighted position, wherein the first weighted position is adapted to scroll through the list of selectable information at a first given scroll rate in a first direction when activated by a user, the second weighted position is adapted to scroll through the list of selectable information at a second given scroll rate in the first direction when activated by a user, and wherein the second given scroll rate is greater than the first given scroll rate;

providing on the scroll element a first intermediate position located between the first weighted position and the second weighted position and adapted to scroll through the list of selectable information in the first direction at a first intermediate given scroll rate that is greater than the first given scroll rate and less than the second given scroll rate; and providing on the scroll element a center position located adjacent to the first weighted position and being adapted to have a scroll rate of zero through the list of selectable information when activated by a user.

15. The method of claim 14, wherein the weighted positions are graphically displayed as separate items.

16. The method of claim 14, wherein the screen is a touch screen, and the scroll element is displayed on the touch screen.

17. The method of claim 14, wherein activation of one of the scroll element weighted positions allows scrolling by a given multiple increment through the list of selectable information.

18. The method of claim 14 further comprising the steps of:
providing on the scroll element a third weighted position and a fourth weighted position, wherein the third weighted position is adapted to scroll through the list of selectable information at a third given scroll rate in a second direction that is opposite to the first direction when activated by a user, the fourth weighted position is adapted to scroll through the list of selectable information at a fourth given scroll rate in the second direction when activated by a user, wherein the fourth given scroll rate is greater than the third given scroll rate; and providing on the scroll element a second intermediate position located between the third weighted position and the fourth weighted position and adapted to scroll through the list of selectable information in the second direction at a second intermediate given scroll rate that is greater than the third given scroll rate and less than the fourth given scroll rate.

19. The method of claim 18 wherein the center position is located between the first weighted position and the third weighted position on the scroll element.

20. A medical pump, comprising:
display screen;
a processing unit in electronic communication with the screen; and
a memory coupled to the processing unit, wherein the memory contains programming code executed by the processing unit for:
supplying a list of selectable information;
displaying only a part of the list of selectable information on the screen, the list of selectable information having a displayed portion and a non-displayed portion;

providing a scroll element adjacent to a viewable portion of the screen, the scroll element being adapted to change the part of the list of selectable information that is the displayed portion by selectively scrolling through the list of selectable information at a variable scrolling rate depending upon a particular position on the scroll element that is activated by a user;

providing on the scroll element a first weighted position and a second weighted position, wherein the first weighted position is adapted to scroll through the list of selectable information at a first given scroll rate in a first direction when activated by a user, the second weighted position is adapted to scroll through the list of selectable information at a second given scroll rate in the first direction when activated by a user, and wherein the second given scroll rate is greater than the first given scroll rate;

providing on the scroll element a first intermediate position located between the first weighted position and the second weighted position and adapted to scroll through the list of selectable information in the first direction at a first intermediate given scroll rate that is greater than the first given scroll rate and less than the second given scroll rate;

providing on the scroll element a center position located adjacent to the first weighted position and being adapted to have a scroll rate of zero through the list of selectable information when activated by a user.

21. The medical pump of claim 20 further comprising:
providing on the scroll element a third weighted position and a fourth weighted position, wherein the third weighted position is adapted to scroll through the list of selectable information at a third given scroll rate in a second direction that is opposite to the first direction when activated by a user, the fourth weighted position is adapted to scroll through the list of selectable information at a fourth given scroll rate in the second direction when activated by a user, wherein the fourth given scroll rate is greater than the third given scroll rate; and providing on the scroll element a second intermediate position located between the third weighted position and the fourth weighted position and adapted to scroll through the list of selectable information in the second direction at a second intermediate given scroll rate that is greater than the third given scroll rate and less than the fourth given scroll rate.

22. The medical pump of claim 21 wherein the center position is located between the first weighted position and the third weighted position on the scroll element.

23. The medical pump of claim 20, wherein the weighted positions are graphically displayed as separate items.

* * * * *